United States Patent
Yanni et al.

(10) Patent No.: US 8,673,873 B1
(45) Date of Patent: Mar. 18, 2014

(54) RNAI-MEDIATED INHIBITION OF PHOSPHODIESTERASE TYPE 4 FOR TREATMENT OF CAMP-RELATED OCULAR DISORDERS

(75) Inventors: John M. Yanni, Burleson, TX (US); Jon E. Chatterton, Fort Worth, TX (US); Daniel A. Gamache, Arlington, TX (US); Steven T. Miller, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 761 days.

(21) Appl. No.: 12/580,663

(22) Filed: Oct. 16, 2009

Related U.S. Application Data

(63) Continuation of application No. 11/617,604, filed on Dec. 28, 2006, now abandoned.

(60) Provisional application No. 60/754,372, filed on Dec. 28, 2005.

(51) Int. Cl.
*C12N 15/11* (2006.01)
*C07H 21/02* (2006.01)
*C12N 15/00* (2006.01)

(52) U.S. Cl.
USPC ............. 514/44 A; 536/24.5; 435/320.6

(58) Field of Classification Search
None
See application file for complete search history.

(56) References Cited

U.S. PATENT DOCUMENTS

| | | | |
|---|---|---|---|
| 6,872,382 B1 * | 3/2005 | Gamache et al. | 424/78.04 |
| 7,056,704 B2 * | 6/2006 | Tuschl et al. | 435/91.1 |
| 7,521,431 B2 * | 4/2009 | Reich et al. | 514/44 R |
| 2003/0045490 A1 * | 3/2003 | Dale et al. | 514/44 |
| 2004/0049022 A1 * | 3/2004 | Nyce et al. | 536/23.2 |
| 2005/0096257 A1 * | 5/2005 | Shima et al. | 514/2 |
| 2007/0031844 A1 | 2/2007 | Khvorova et al. | |

OTHER PUBLICATIONS

Barber et al (Am J Physiol Lung Cell Mol Physiol 287:332-343, 2004), Nyce et al (US 20040049022).*
D.H. Kim, et al., "Synthetic dsRNA dicer substrates enhance RNAi potency and efficacy", Nat. Biotechnol. (2005); pp. 222-226; 23(2).
S.F. Altschul, et al.; "Blastin"; J. Mol. Biol. (1990); pp. 403-410; 215.
J.P. Gilbard, et al., "Stimulation of Tear Secretion by Topical Agents That Increase Cyclic Nucleotide Levels"; IVOS; (Jul. 1990); vol. 31, No. 7; pp. 1381-1388.
D. Castanotto, et al., "Functional siRNA Expression from Transfected PCR Products"; RNAJournal.org; (2002); 8:1454-1460.
T.R. Brummelkamp, et al.; "A System for Stable Expression of Short Interfering RNAs in Mammalian Cells"; Sciencemag.org; (Apr. 19, 2002); vol. 296; pp. 550-553.

* cited by examiner

*Primary Examiner* — Richard Schnizer

(57) ABSTRACT

RNA interference is provided for inhibition of phosphodiesterase type 4 mRNA expression for treating patients with a cAMP-related ocular disorder. Phosphodiesterase type 4 mRNA targets include mRNA for 4A, 4B, 4C, and 4D phosphodiesterase isoforms.

6 Claims, 1 Drawing Sheet

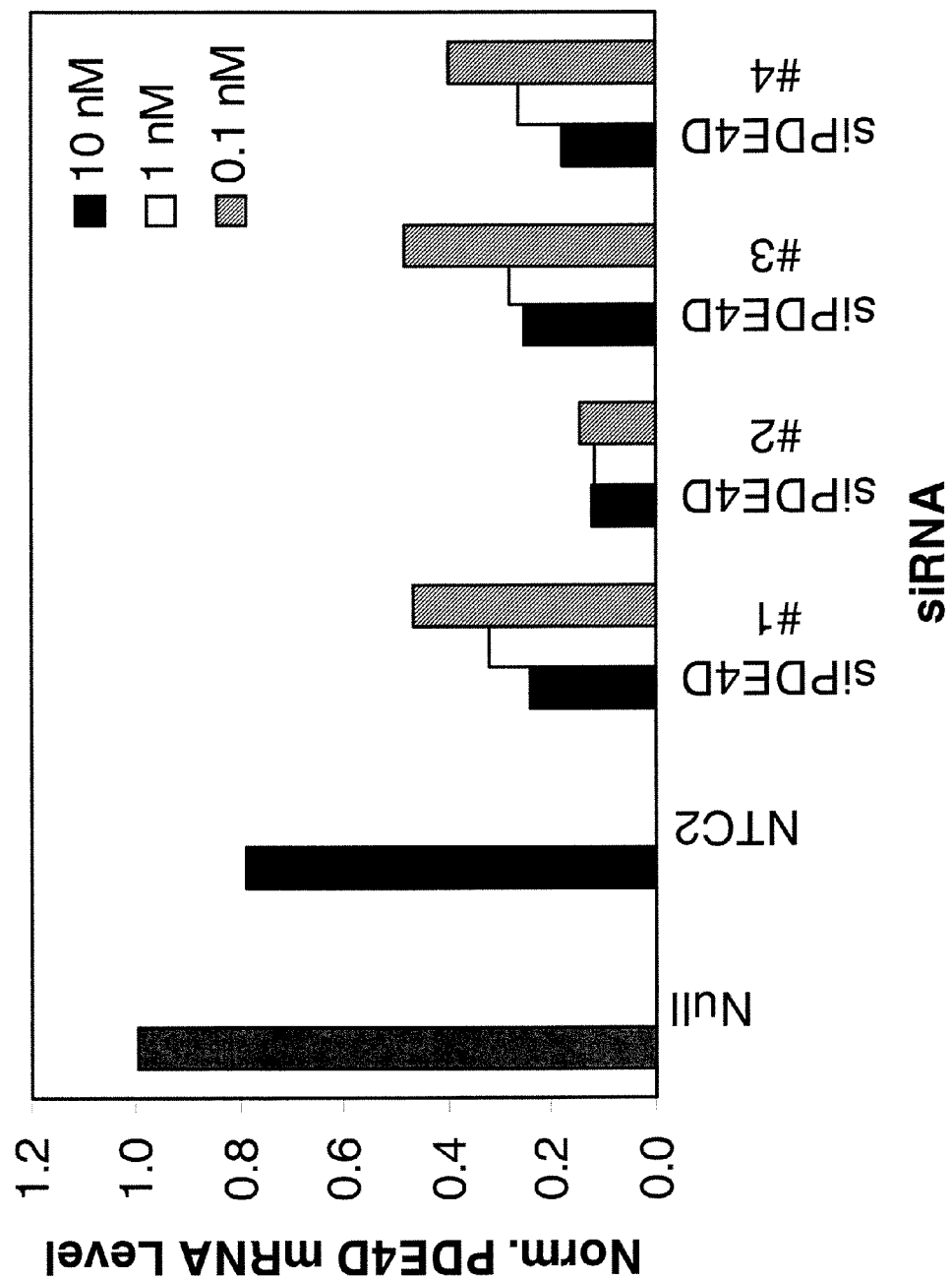

SEQUENCE LISTING

```
<160> NUMBER OF SEQ ID NOS: 207

<210> SEQ ID NO 1
<211> LENGTH: 4255
<212> TYPE: DNA
<213> ORGANISM: Homo sapiens

<400> SEQUENCE: 1
cagcctcctc ctgggaccct tgccctgccc ccctcccatg ggcacggacc ccccaccgcc      60
tccacccact gccgcggggg ggcccgttgg ggcccagggc tggcgggcca tgtaaccagg     120
gctgctgctg ggagcgcgga ggggaaggga gccccagcc ctgctgggcc ggcccaggcc     180
```

```
cctccgcggc tccccctcc actacccacc tgcccggcac cccctcccca gtggttgtta     240
accccgggac tccccaagcc cagcctctgt gtgcagcagc cccaggcggg ctaagtctcc     300
aagatgccct tggtggattt cttctgcgag acctgctcta agccttggct ggtgggctgg     360
tgggaccagt tcaaaaggat gttgaaccgt gagctcacac acctgtcaga aatgagcagg     420
tccggaaacc aggtctcaga gtacatttcc acaacattcc tggacaaaca gaatgaagtg     480
gagatcccat cacccacgat gaaggaacga gaaaaacagc aagcgccgcg accaagaccc     540
tcccagccgc cccgccccc  tgtaccacac ttacagccca tgtcccaaat cacagggttg     600
aaaaagttga tgcatagtaa cagcctgaac aactctaaca ttccccgatt tggggtgaag     660
accgatcaag aagagctcct ggcccaagaa ctggagaacc tgaacaagtg gggcctgaac     720
atcttttgcg tgtcggatta cgctggaggc cgctcactca cctgcatcat gtacatgata     780
ttccaggagc gggacctgct gaagaaattc cgcatccctg tggacacgat ggtgacatac     840
atgctgacgc tggaggatca ctaccacgct gacgtggcct accataacag cctgcacgca     900
gctgacgtgc tgcagtccac ccacgtactg ctggccacgc ctgcactaga tgcagtgttc     960
acggacctgg agattctcgc cgccctcttc gcggctgcca tccacgatgt ggatcaccct    1020
ggggtctcca accagttcct catcaacacc aattcggagc tggcgctcat gtacaacgat    1080
gagtcggtgc tcgagaatca ccacctggcc gtgggcttca agctgctgca ggaggacaac    1140
tgcgacatct tccagaacct cagcaagcgc cagcggcaga gcctacgcaa gatggtcatc    1200
gacatggtgc tggccacgga catgtccaag cacatgaccc tcctggctga cctgaagacc    1260
atggtggaga ccaagaaagt gaccagctca ggggtcctcc tgctagataa ctactccgac    1320
cgcatccagg tcctccggaa catggtgcac tgtgccgacc tcagcaaccc caccaagccg    1380
ctggagctgt accgccagtg gacagaccgc atcatggccg agttcttcca gcagggtgac    1440
cgagagcgcg agcgtggcat ggaaatcagc cccatgtgtg acaagcacac tgcctccgtg    1500
gagaagtctc aggtgggttt tattgactac attgtgcacc cattgtggga gacctgggcg    1560
gaccttgtcc acccagatgc ccaggagatc ttggacactt tggaggacaa ccgggactgg    1620
tactacagcg ccatccggca gagcccatct ccgccaccccg aggaggagtc aagggggcca    1680
ggccacccac ccctgcctga caagttccag tttgagctga cgctggagga ggaagaggag    1740
gaagaaatat caatggccca gataccgtgc acagcccaag aggcattgac tgcgcaggga    1800
ttgtcaggag tcgaggaagc tctggatgca accatagcct gggaggcatc cccggcccag    1860
gagtcgttgg aagttatggc acaggaagca tccctggagg ccgagctgga ggcagtgtat    1920
ttgacacagc aggcacagtc cacaggcagt gcacctgtgg ctccggatga gttctcgtcc    1980
cgggaggaat tcgtggttgc tgtaagccac agcagcccct ctgccctggc tcttcaaagc    2040 cccccttctcc ctgcttggag gaccctgtct gtttcagagc atgccccggg cctcccgggc    2100 ctccccctcca cggcggccga ggtggaggcc aacgagagc accaggctgc caagagggct    2160
tgcagtgcct gcgcagggac atttggggag gacacatccg cactcccagc tcctggtggc    2220 gggggggtcag gtggagaccc tacctgatcc ccagacctct gtccctgttc ccctccactc    2280
ctcccctcac tccctgctc  ccccgaccac ctcctcctct gcctcaaaga ctcttgtcct    2340
cttgtccctc ctgagaaaaa agaaaacgaa aagtgggtt  ttttctgtt  ttctttttt    2400 cccctttccc cctgccccca cccacggggc cttttttggg aggtggggc  tgggaatga     2460 ggggctgagg tcccggaagg atttttatttt tttgaattt  aattgtaaca tttttagaaa    2520
aagaacaaaa aaagaaaaaa aaaagaaaga aacacagcaa ctgtagatgc tcctgttcct    2580
```

-continued

```
ggttcccgct ttccacttcc aaatccctcc cctcaccttc ccccactgcc ccccaagttc      2640
caggctcagt cttccagccg cctggggagt ctctacctgg gcccaagcag gtgtggggcc      2700
tccttctggg cttttcttct gaatttagag gatttctaga acgtggtcag gaatagccat      2760
tctaggcggg gctggggcca gggtgggggg cagtcactgt gggaggtccc agctccagcc      2820
cccctctggt ttgctgcctc ctctcccctc taaaaaagtc ttccgcttga ttttgcacaa      2880
tcccggcgat actcctggcg atactgacta gaaagtcagg gagctggggg agctgttcac      2940
tttaggatac gggggtggta tggaagggag cgttcacacc gccagcctcg ggcctgggat      3000
ttgaggaggg ccctagacct cctccactct ccatccccct tcccttccac tttgggttca      3060
ctttgaattt tctccgtttt ttggggcagt ggctctgatc cactcacccc cccgcccccc      3120
gccccacttc tagctgcttc tcctcttgtt tctgccttaa taattcccac ggccacaggc      3180
aagggggttg cagtggccgc ctgcaccttg gatgaggcag ggccaggcgc ccagaacccc      3240
catcctggcc gcaccccect ttccagggtc tccggaccc caccttccac actctgatca      3300
cagcccccct accttttgcc ctaggaggaa gcaataatgg tgtatacccct cattctcatt      3360 cctgggcagc ccttccttcc accctggcac caaaataatt tctcctccat ccgtaccttg      3420
cctagcctct ccctctcccc cagctagtcc cctgagcaat acggcagaca gatgcaagac      3480
catttttctc caagccatgg gggactgttt ggaaggaaag cccctctct ccctcctccc      3540 ctcgccctcg gcctggttct gcagctggac cgacctcatt catcgcctgc ccctaccca      3600 attctgagca cacggtactg tagccccag ttcctccta gccttccatc cctctgtcca      3660
ccccaggggg aggtaacccc gcactcacac tcccttgatg ctgtctgtac agggttcata      3720
ttttgtagcg aaagtcgttt ttgtcccagc cggcgatcgg agtgggcctt ttctttcttt      3780
ttgttcattc tttaccttttt tttctttct ttctttcttt tttgtacata ctgtaaggtt      3840
ggtttgtaaa ttattctacg gaggcaaaaa gggaaaataa aaacttgccc ttccctggct      3900
gacccagtcg ggaaggtagg gaaggaggtc tcccgttggg agagtctctg ttcctgctgt      3960
attatacaac tgtaccatag tcctgggaaa agggtggact caccgctgtt gttttatggg      4020
aagtcgtgtc atcctagggg ttggggctgg gcagagcctg tccccctcccc ccttctccag      4080 gagccagggg gtgactggag agacagaccc accccaagc agggctcctc tccccagggt      4140
gagcacagga cctctgtaag ctgccttgtgt attgtccact ttgacgatca gtcattcggt      4200
ccgttgatca ataatccttc gatcttgtct ccaattaaac cgaggctttc accga         4255
```

<210> SEQ ID NO 2
<211> LENGTH: 4264
<212> TYPE: DNA
<213> ORGANISM: Homo sapiens

<400> SEQUENCE: 2

```
agagcgctgc ggccgcggcg gtgcagcaga ggcgcctcgg gcaggaggag ggcggcttct        60
gcgagggcag cctgaggtat taaaaagtgt cagcaaactg cattgaataa cagacatcct       120 aagagggat atttttccacc tctataatga agaaaagcag gagtgtgatg acggtgatgg       180
ctgatgataa tgttaaagat tatttttgaat gtagcttgag taaatcctac agttcttcca       240
gtaacacact tgggatcgac ctctggagag ggagaaggtt ttgctcagga aacttacagt       300
taccaccact gtctcaaaga cagagtgaaa gggcaaggac tcctgaggga gatggtattt       360
ccaggccgac cacactgcct ttgacaacgc ttccaagcat tgctattaca actgtaagcc       420
aggagtgctt tgatgtggaa aatggcccctt ccccaggtcg gagtccactg gatccccagg       480
```

```
ccagctcttc cgctgggctg gtacttcacg ccacctttcc tgggcacagc cagcgcagag    540
agtcatttct ctacagatca gacagcgact atgacttgtc accaaaggcg atgtcgagaa    600
actcttctct tccaagcgag caacacggcg atgacttgat tgtaactcct tttgcccagg    660
tccttgccag cttgcgaagt gtgagaaaca acttcactat actgacaaac cttcatggta    720
catctaacaa gaggtcccca gctgctagtc agcctcctgt ctccagagtc aacccacaag    780
aagaatctta tcaaaaatta gcaatggaaa cgctggagga attagactgg tgtttagacc    840
agctagagac catacagacc taccggtctg tcagtgagat ggcttctaac aagttcaaaa    900
gaatgctgaa ccgggagctg acacacctct cagagatgag ccgatcaggg aaccaggtgt    960
ctgaatacat ttcaaatact ttcttagaca agcagaatga tgtggagatc ccatctccta   1020
cccagaaaga cagggagaaa aagaaaaagc agcagctcat gacccagata agtggagtga   1080
agaaattaat gcatagttca agcctaaaca atacaagcat ctcacgcttt ggagtcaaca   1140
ctgaaaatga agatcacctg gccaaggagc tggaagacct gaacaaatgg ggtcttaaca   1200
tctttaatgt ggctggatat tctcacaata gaccccctaac atgcatcatg tatgctatat   1260
tccaggaaag agacctccta aagacattca gaatctcatc tgacacattt ataacctaca   1320
tgatgacttt agaagaccat taccattctg acgtggcata tcacaacagc ctgcacgctg   1380
ctgatgtagc ccagtcgacc catgttctcc tttctacacc agcattagac gctgtcttca   1440
cagatttgga gatcctggct gccattttg cagctgccat ccatgacgtt gatcatcctg   1500
gagtctccaa tcagttttctc atcaacacaa attcagaact tgctttgatg tataatgatg   1560
aatctgtgtt ggaaaatcat caccttgctg tgggtttcaa actgctgcaa gaagaacact   1620
gtgacatctt catgaatctc accaagaagc agcgtcagac actcaggaag atggttattg   1680
acatggtgtt agcaactgat atgtctaaac atatgagcct gctggcagac ctgaagacaa   1740
tggtagaaac gaagaaagtt acaagttcag gcgttcttct cctagacaac tataccgatc   1800
gcattcaggt ccttcgcaac atggtacact gtgcagacct gagcaacccc accaagtcct   1860
tggaattgta tcggcaatgg acagaccgca tcatggagga attttccag cagggagaca   1920 aagagcggga gaggggaatg gaaattagcc caatgtgtga taacacaca gcttctgtgg   1980 aaaaatccca ggttggtttc atcgactaca ttgtccatcc attgtgggag acatgggcag   2040
atttggtaca gcctgatgct caggacattc tcgataccttt agaagataac aggaactggt   2100
atcagagcat gataccctcaa agtccctcac caccactgga cgagcagaac agggactgcc   2160
agggtctgat ggagaagttt cagtttgaac tgactctcga tgaggaagat tctgaaggac   2220
ctgagaagga gggagaggga cacagctatt tcagcagcac aaagacgctt tgtgtgattg   2280
atccagaaaa cagagattcc ctgggagaga ctgacataga cattgcaaca gaagacaagt   2340
cccccgtgga tacataatcc ccctctccct gtggagatga acattctatc cttgatgagc   2400
atgccagcta tgtggtaggg ccagcccacc atggggccca agacctgcac aggacaaggg   2460
ccacctggcc tttcagttac ttgagtttgg agtcagaaag caagaccagg aagcaaatag   2520
cagctcagga aatcccacgg ttgacttgcc ttgatggcaa gcttggtgga gagggctgaa   2580
gctgttgctg ggggccgatt ctgatcaaga cacatggctt gaaaatggaa gacacaaaac   2640
tgagagatca ttctgcacta agtttcggga acttatcccc gacagtgact gaactcactg   2700
actaataact tcatttatga atcttctcac ttgtcccttt gtctgccaac ctgtgtgcct   2760
tttttgtaaa acattttcat gtcttttaaaa tgcctgttga atacctggag tttagtatca   2820
acttctacac agataagctt tcaaagttga caaacttttt tgactctttc tggaaaaggg   2880
```

-continued

| | |
|---|---|
| aaagaaaata gtcttccttc tttcttgggc aatatccttc actttactac agttactttt | 2940 |
| gcaaacagac agaaaggata cacttctaac cacatttac ttccttcccc tgttgtccag | 3000 |
| tccaactcca cagtcactct taaaacttct ctctgtttgc ctgcctccaa cagtactttt | 3060 |
| aacttttgc tgtaaacaga ataaaattga acaaattagg gggtagaaag gagcagtggt | 3120 |
| gtcgttcacc gtgagagtct gcatagaact cagcagtgtg ccctgctgtg tcttggaccc | 3180 |
| tgcccccac aggagttgta cagtccctgg ccctgttccc tacctcctct cttcaccccg | 3240 |
| ttaggctgtt ttcaatgtaa tgctgccgtc cttctcttgc actgccttct gcgctaacac | 3300 |
| ctccattcct gttataacc gtgtatttat tacttaatgt atataatgta atgttttgta | 3360 |
| agttattaat ttatatatct aacattgcct gccaatggtg gtgttaaatt tgtgtagaaa | 3420 |
| actctgccta agagttacga cttttcttg taatgttttg tattgtgtat tatataaccc | 3480 |
| aaacgtcact tagtagagac atatggcccc cttggcagag aggacagggg tgggcttttg | 3540 |
| ttcaaagggt ctgcccttc cctgcctgag ttgctacttc tgcacaaccc ctttatgaac | 3600 |
| cagttttgga aacaatattc tcacattaga tactaaatgg tttatactga gcttttactt | 3660 |
| ttgtatagct tgatagggc aggggcaat gggatgtagt ttttacccag gttctatcca | 3720 |
| aatctatgtg ggcatgagtt gggttataac tggatcctac tatcattgtg gctttggttc | 3780 |
| aaaaggaaac actacatttg ctcacagatg attcttctga atgctcccga actactgact | 3840 |
| ttgaagaggt agcctcctgc ctgccattaa gcaggaatgt catgttccag ttcattacaa | 3900 |
| aagaaaacaa taaacaatg tgaattttta taataaatg tgaactgatg tagcaaatta | 3960 |
| cgcaaatgtg aagcctcttc tgataacact tgttaggcct cttactgatg tcagtttcag | 4020 |
| tttgtaaaat atgtttcatg ctttcagttc agcattgtga ctcagtaatt acagaaaatg | 4080 |
| gcacaaatgt gcatgaccaa tgtatgtcta tgaacactgc attgtttcag gtggacattt | 4140 |
| tatcattttc aaatgtttct cacaatgtat gttatagtat tattattata tattgtgttc | 4200 |
| aaatgcattc taaagagact tttatatgag gtgaataaag aaaagcatga ttagattaaa | 4260 |
| aaaa | 4264 |

<210> SEQ ID NO 3
<211> LENGTH: 3495
<212> TYPE: DNA
<213> ORGANISM: Homo sapiens

<400> SEQUENCE: 3

| | |
|---|---|
| ccagtctgcg gaccgttcgg agcaacgtgg cggcccttgc ccgccagcaa tgcctaggag | 60 |
| cagccaagca gggacccgtc ggaaaccctt catccagcct ttctctggcg catggagaac | 120 |
| ctggggtcg gcgaagggc agaggcttgc agcaggttga gtcgctctcg cggccgccac | 180 |
| agcatgacca gagccccgaa gcacctgtgg cggcaacccc ggcgcccat ccgcatccaa | 240 |
| cagcgcttct attcggatcc ggacaagtcc gcgggctgcc gcgagaggga cctgagcccg | 300 |
| cggccggagc tcaggaagtc gcggctctcc tggcccgttt cctcctgcag gcgctttgac | 360 |
| ctggaaaatg ggctctcgtg tgggaggagg ccctggacc tcagtccag ccctggcctg | 420 |
| ggccggatta tgcaggctcc agtcccgcac agccagcggc gcgagtcctt cctgtaccgc | 480 |
| tcagatagcg actatgaact ctcgcccaag gccatgtctc ggaactcctc tgtggccagc | 540 |
| gacctacatg gagaggacat gattgtgacg cccttgccc aggtcctggc cagtctgcgg | 600 |
| accgttcgga gcaacgtggc ggcccttgcc cgccagcaat gcctaggagc agccaagcag | 660 |
| ggacccgtcg gaaaccctc atccagcaat cagctccctc ctgcagagga cacgggggcag | 720 |

```
aagctggcat tggagacgct agacgagctg gactggtgcc tggatcagtt ggagacgctg    780
cagacccggc actcggtggg ggagatggcc tccaacaagt tcaagcggat cctgaaccgg    840
gagttgaccc acctgtccga aaccagccgc tccgggaacc aggtgtccga gtacatctcc    900
cggaccttcc tggaccagca gaccgaggtg gagctgccca aggtgaccgc tgaggaggcc    960
ccacagccca tgtcccggat cagtggccta catgggctct gccacagtgc cagcctctcc   1020
tcagccactg tcccacgctt tggggtccag actgaccagg aggagcaact ggccaaggag   1080
ctagaagaca ccaacaagtg gggacttgat gtgttcaagg tggcggacgt aagtgggaac   1140
cggcccctca cagctatcat attcagcatt tttcaggagc gggacctgct gaagacattc   1200
cagatcccag cagacacact ggccacctac ctgctgatgc tggagggtca ctaccacgcc   1260
aatgtggcct accacaacag cctacatgcc gccgacgtgg cccagtccac gcatgtgctg   1320
ctggctacgc ccgccctcga ggctgtgttc acagacttgg aaatcctggc tgccctcttt   1380
gcaagcgcca tccacgacgt ggaccatcct ggggtctcca accagtttct gattaacacc   1440
aactcagacg tggcgcttat gtacaacgac gcctcggtgc tggagaacca tcacctggct   1500
gtgggcttca agctgctgca ggcagagaac tgcgatatct tccagaacct cagcgccaag   1560
cagcgactga gtctgcgcag gatggtcatt gacatggtgc tggccacaga catgtccaaa   1620
cacatgaacc tcctggccga cctcaagacc atggtggaga ccaagaaggt gacaagcctc   1680
ggtgtcctcc tcctggacaa ctattccgac cgaatccagg tcttgcagaa cctggtgcac   1740
tgtgctgatc tgagcaaccc caccaagccg ctgcccctgt accgcagtg dacggaccgc   1800 atcatggccg agttcttcca gcaggagac cgcgagcgtg agtcgggcct ggacatcagt   1860
cccatgtgtg acaagcatac ggcctcagtg gagaagtccc aggtgggttt cattgactac   1920
attgctcacc cactgtggga cttgggct gacctggtcc acccagatgc acaggacctg   1980
ctggacacgc tggaggacaa tcgagagtgg taccagagca agatccccg aagtccctca   2040 gacctcacca accccgagcg ggacgggcct gacagattcc agtttgaact gactctggag   2100
gaggcagagg aagaggatga ggaggaagaa gaggaggggg aagagacagc tttagccaaa   2160
gaggccttgg agttgcctga cactgaactc ctgtccctg aagccggccc agaccctggg   2220
gacttacccc tcgacaacca gaggacttag ggccagccct gcgtgaactg caggggcaat   2280
ggatggtaaa gcccttggc tcttggcagg cagactttcc aggaagaggc tccatgtggc   2340
tcctgcttca ctttcccacc catttaggga gacaatcaag ctcttagtta taggtggctc   2400
ccagggtcta attggaggca cctggctggg gtccactctg acccctagact tgcctaaaag   2460 agctctctaa ggggcagcct cttacgatgc cctggtgtct ttctcctggg cttctatccc   2520
tgtgaggaga ggtgctgtct gctggagcct ctagtccacc ctctccagtg gtcactcttg   2580
agtcacatct gtcacttaat tatttccttc tttatcaaat atttattgct catctacttc   2640
gggccagctt tctgcctctg tagtagccct gcacaaaggg tggggagtca ggagaccatc   2700
ccaaaggcat ctccctgtct tcctctacca gcggctctc tgcaagagca tggaaatgtg   2760 agtgggaaa atttttcagca ccaaagcttc actcataccc agttttgttt ctgaaactac   2820 ggtaggggc aggaagagga gcagaaaaga agggctgggc aaggcatagt ggcttatgcc   2880
tgtaatcccg gtactttggg aggctgaggt gggaggactg cttaagctca ggagtttgag   2940
accagcctgg gcaacatagc aagaccccca ccatctctga aaaaaaaaat tagccaggca   3000
tggtggtgtg cacctgagaa tcccagctac tcagaaggtt gagacaaagg ggatcgcttg   3060
agcccaggag ttggaggctg aagagagcta tgactgcatc actgcactcc agcctgggca   3120
```

```
acacagcaag atcctgtcta aaaataaaaa gaaagagaa  ggaaaggaaa gagacggggc    3180
tctgaggccg agcacagtgg cccatgccta taatcccagc actttgggag gctgaggcag    3240
gtggatcacc tgaggttagg agttcgagac cagcctggcc aacatggtga accccatct    3300 ctactaaaaa tacaaaaatt ggctgggcat ggtggcgggt gcctgtaatc ccagctactg    3360
gggaggctga ggcaggagaa tcacttgaat tcaggaggtg gaggttgcag tgagccgaca    3420
tcatgccact gcactccagc ctggggctga cagagcaaga cactgtctca aaaagaaaa    3480 aaaaaaaaaa aaaaa                                                    3495

<210> SEQ ID NO 4
<211> LENGTH: 5876
<212> TYPE: DNA
<213> ORGANISM: Homo sapiens

<400> SEQUENCE: 4
ggaattcatc tgtaaaaatc actacatgta acgtaggaga caagaaaaat attaatgaca      60
gaagatctgc gaacatgatg cacgtgaata attttcccct tagaaggcat tcctggatat     120
gttttgatgt ggacaatggc acatctgcgg gacggagtcc cttggatccc atgaccagcc     180
caggatccgg gctaattctc caagcaaatt ttgtccacag tcaacgacgg gagtccttcc     240
tgtatcgatc cgacagcgat tatgacctct ctccaaagtc tatgtcccgg aactcctcca     300
ttgccagtga tatacacgga gatgacttga ttgtgactcc atttgctcag gtcttggcca     360
gtctgcgaac tgtacgaaac aactttgctg cattaactaa tttgcaagat cgagcaccta     420
gcaaaagatc acccatgtgc aaccaaccat ccatcaacaa agccaccata acagaggagg     480
cctaccagaa actggccagc gagacctggg aggagctgga ctggtgtctg accagctag      540 agaccctaca gaccaggcac tccgtcagtg agatggcctc caacaagttt aaaaggatgc     600
ttaatcggga gctcacccat ctctctgaaa tgagtcggtc tggaaatcaa gtgtcagagt     660
ttatatcaaa cacattctta gataagcaac atgaagtgga aattccttct ccaactcaga     720
aggaaaagga gaaaagaaa agaccaatgt ctcagatcag tggagtcaag aaattgatgc      780
acagctctag tctgactaat tcaagtatcc caaggtttgg agttaaaact gaacaagaag     840
atgtccttgc caaggaacta aagatgtga acaaatgggg tcttcatgtt ttcagaatag      900
cagagttgtc tggtaaccgg ccttgactg ttatcatgca caccattttt caggaacggg      960
atttattaaa acatttaaa attccagtag atactttaat tacatatctt atgactctcg     1020
aagaccatta ccatgctgat gtggcctatc acaacaatat ccatgctgca gatgttgtcc    1080
agtctactca tgtgctatta tctacacctg ctttggaggc tgtgtttaca gatttggaga    1140
ttcttgcagc aatttttgcc agtgcaatac atgatgtaga tcatcctggt gtgtccaatc    1200
aatttctgat caatacaaac tctgaacttg ccttgatgta caatgattcc tcagtcttag    1260
agaaccatca tttggctgtg gcttaaat tgcttcagga gaaaactgt gacatttcc        1320 agaatttgac caaaaacaa agacaatctt taaggaaaat ggtcattgac atcgtacttg     1380
caacagatat gtcaaacac atgaatctac tggctgattt gaagactatg ttgaaacta      1440 agaaagtgac aagctctgga gttcttcttc ttgataatta ttccgatagg attcaggttc    1500
ttcagaatat ggtgcactgt gcagatctga gcaacccaac aaagcctctc cagctgtacc    1560
gccagtggac ggaccggata tggaggagt tcttccgcca aggagaccga gagggaac       1620 gtggcatgga gataagcccc atgtgtgaca agcacaatgc ttccgtggaa aaatcacagg    1680
tgggcttcat agactatatt gttcatcccc tctgggagac atgggcagac ctcgtccacc    1740
```

```
ctgacgccca ggatattttg gacactttgg aggacaatcg tgaatggtac cagagcacaa      1800
tccctcagag cccctctcct gcacctgatg acccagagga gggccggcag ggtcaaactg      1860
agaaattcca gtttgaacta actttagagg aagatggtga gtcagacacg gaaaaggaca     1920
gtggcagtca agtggaagaa gacactagct gcagtgactc caagactctt tgtactcaag     1980
actcagagtc tactgaaatt ccccttgatg aacaggttga agaggaggca gtaggggaag     2040
aagaggaaag ccagcctgaa gcctgtgtca tagatgatcg ttctcctgac acgtaacagt     2100
gcaaaaactt tcatgccttt tttttttta agtagaaaaa ttgtttccaa agtgcatgtc      2160
acatgccaca accacggtca cacctcactg tcatctgcca ggacgtttgt tgaacaaaac     2220
tgaccttgac tactcagtcc agcgctcagg aatatcgtaa ccagtttttt cacctccatg     2280
tcatccgagc aaggtggaca tcttcacgaa cagcgttttt aacaagattt cagcttggta     2340
gagctgacaa agcagataaa atctactcca aattattttc aagagagtgt gactcatcag     2400
gcagcccaaa agtttattgg acttggggtt tctattcctt tttatttgtt tgcaatattt     2460
tcagaagaaa ggcattgcac agagtgaact taatggacga agcaacaaat atgtcaagaa     2520
caggacatag cacgaatctg ttaccagtag gaggaggatg agccacagaa attgcataat     2580
tttctaattt caagtcttcc tgatacatga ctgaatagtg tggttcagtg agctgcactg     2640
acctctacat tttgtatgat atgtaaaaca gattttttgt agagcttact tttattatta     2700
aatgtattga ggtattatat ttaaaaaaaa ctatgttcag aacttcatct gccactggtt     2760
atttttttct aaggagtaac ttgcaagttt tcagtacaaa tctgtgctac actggataaa     2820
aatctaattt atgaatttta cttgcacctt atagttcata gcaattaact gatttgtagt     2880
gattcattgt ttgttttata taccaatgac ttccatattt taaaagagaa aaacaacttt     2940
atgttgcagg aaacccttt tgtaagtctt tattatttac tttgcatttt gtttcactct      3000
ttccagataa gcagagttgc tcttcaccag tgttttctt catgtgcaaa gtgactattt       3060
gttctataat acttttatgt gtgttatatc aaatgtgtct taagcttcat gcaaactcag     3120
tcatcagttc gtgttgtctg aagcaagtgg gaaatatata aatacccagt agctaaaatg     3180
gtcagtcttt tttagatgtt ttcctactta gtatctccta ataacgtttt gctgtgtcac     3240
tagatgttca tttcacaagt gcatgtcttt ctaataatcc acacatttca tgctctaata     3300
atccacacat ttcatgctca ttttttattgt ttttacagcc agttatagca agaaaaaggt     3360 ttttccccctt gtgctgcttt ataatttagc gtgtgtctga accttatcca tgtttgctag    3420
atgaggtctt gtcaaatata tcactaccat tgtcaccggt gaaagaaac aggtagttaa      3480 gttagggtta acattcattt caaccacgag gttgtatatc atgactagct tttactcttg     3540
gtttacagag aaaagttaaa caaccaacta ggcagttttt aagaatatta acaatatatt     3600
aacaaacacc aatacaacta atcctatttg gttttaatga tttcaccatg ggattaagaa     3660
ctatatcagg aacatccctg agaaacggct ttaagtgtag caactactct tccttaatgg     3720
acagccacat aacgtgtagg aagtccttta tcacttatcc tcgatccata agcatatctt     3780
gcagagggga actacttctt taaacacatg gagggaaaga agatgatgcc actggcacca     3840
gagggttagt actgtgatgc atcctaaaat atttattata ttggtaaaaa ttctggttaa     3900
ataaaaaatt agagatcact cttggctgat ttcagcacca ggaactgtat tacagttta      3960 gagattaatt cctagtgttt acctgattat agcagttggc atcatggggc atttaattct     4020
gactttatcc ccacgtcagc cttaataaag tcttctttac cttctctatg aagacttaa      4080 agcccaaata atcatttttc acattgatat tcaagaattg agatagatag aagccaaagt     4140
```

-continued

```
gggtatctga caagtggaaa atcaaacgtt taagaagaat tacaactctg aaaagcattt    4200
atatgtggaa cttctcaagg agcctcctgg ggactggaaa gtaagtcatc agccaggcaa    4260
atgactcatg ctgaagagag tccccatttc agtccctga  gatctagctg atgcttagat    4320
cctttgaaat aaaaattatg tctttataac tctgatcttt tacataaagc agaagaggaa    4380
tcaactagtt aattgcaagg tttctactct gtttcctctg taaagatcag atggtaatct    4440
ttcaaataag aaaaaaataa agacgtatgt ttgaccaagt agtttcacaa gaatatttgg    4500
gaacttgttt cttttaattt tatttgtccc tgagtgaagt ctagaaagaa aggtaaagag    4560
tctagagttt attcctcttt ccaaaacatt ctcattcctc tcctccctac acttagtatt    4620
tcccccacag agtgcctaga atcttaataa tgaataaaat aaaaagcagc aatatgtcat    4680
taacaaatcc agacctgaaa gggtaaaggg tttataactg cactaataaa gagaggctct    4740
ttttttttct tccagtttgt tggttttttaa tggtaccgtg ttgtaaagat acccactaat    4800
ggacaatcaa attgcagaaa aggctcaata tccaagagac agggactaat gcactgtaca    4860
atctgcttat ccttgccctt ctctcttgcc aaagtgtgct tcagaaatat atactgcttt    4920
aaaaaagaat aaaagaatat cctttttacaa gtggctttac atttcctaaa atgccataag    4980
aaaatgcaat atctgggtac tgtatgggga aaaaaatgtc caagtttgtg taaaaccagt    5040
gcatttcagc ttgcaagtta ctgaacacaa taatgctgtt ttaattttgt tttatatcag    5100
ttaaaattca caataatgta gatagaacaa attacagaca aggaaagaaa aaacttgaat    5160
gaaatggatt ttacagaaag ctttatgata attttttgaat gcattattta tttttttgtgc   5220 catgcatttt ttttctcacc aaatgacctt acctgtaata cagtcttgtt tgtctgttta    5280
caaccatgta tttattgcaa tgtacatact gtaatgttaa ttgtaaatta tctgttctta    5340
ttaaaacatc atcccatgat ggggtggtgt tgatatattt ggaaactctt ggtgagagaa    5400
tgaatggtgt gtatacatac tctgtacatt tttctttctt cctgtaatat agtcttgtca    5460
ccttagagct tgtttatgga agattcaaga aaactataaa atacttaaag atatataaat    5520
ttaaaaaaac atagctgcag gtctttggtc ccagggctgt gccttaactt taaccaatat    5580
tttcttctgt tttgctgcat ttgaaaggta acagtggagc tagggctggg catttttacat   5640 ccaggctttt aattgattag aattctgcca ataggtggat tttacaaaac cacagacaac    5700
ctctgaaaga ttctgagacc cttttgagac agaagctctt aagtacttct tgccagggag    5760
cagcactgca tgtgtgatgg ttgtttgcca tctgttgatc aggaactact tcagctactt    5820
gcatttgatt atttccttt  tttttttttt taactcggaa acacaactgg gggaat        5876
```

<210> SEQ ID NO 5
<211> LENGTH: 19
<212> TYPE: DNA
<213> ORGANISM: Artificial
<220> FEATURE:
<223> OTHER INFORMATION: Target sequence

<400> SEQUENCE: 5
aaaggatgtt gaaccgtga                                                  19

<210> SEQ ID NO 6
<211> LENGTH: 21
<212> TYPE: DNA
<213> ORGANISM: Artificial
<220> FEATURE:
<223> OTHER INFORMATION: Sense strand with 3'NN
<220> FEATURE:
<221> NAME/KEY: misc_RNA
<222> LOCATION: (1)..(19)

```
<223> OTHER INFORMATION: Ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 6
aaaggauguu gaaccgugan n                                              21

<210> SEQ ID NO 7
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: Ribonucleotides
<220> FEATURE:
<221> NAME/KEY: misc_feature
<222> LOCATION: (20)..(21)
<223> OTHER INFORMATION: any, A, T/U, C, G

<400> SEQUENCE: 7
ucacgguuca acauccuuun n                                              21

<210> SEQ ID NO 8
<211> LENGTH: 21
<212> TYPE: RNA
<213> ORGANISM: Artificial
<220> FEATURE:
<223> OTHER INFORMATION: Sense strand

<400> SEQUENCE: 8
aaaggauguu gaaccgugau u                                              21

<210> SEQ ID NO 9
<211> LENGTH: 21
<212> TYPE: RNA
<213> ORGANISM: Artificial
<220> FEATURE:
<223> OTHER INFORMATION: Antisense strand

<400> SEQUENCE: 9
ucacgguuca acauccuuuu u                                              21

<210> SEQ ID NO 10
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: Ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: Ribonucleotides

<400> SEQUENCE: 10
aaaggauguu gaaccgugan nnnnnnnuca cgguucaaca uccuuuuu                 48

<210> SEQ ID NO 11
```

```
<211> LENGTH: 19
<212> TYPE: DNA
<213> ORGANISM: Artificial
<220> FEATURE:
<223> OTHER INFORMATION: Target sequence

<400> SEQUENCE: 11
ctcacacacc tgtcagaaa                                               19

<210> SEQ ID NO 12
<211> LENGTH: 19
<212> TYPE: DNA
<213> ORGANISM: Artificial
<220> FEATURE:
<223> OTHER INFORMATION: Target sequence

<400> SEQUENCE: 12
tcacacacct gtcagaaat                                               19

<210> SEQ ID NO 13
<211> LENGTH: 19
<212> TYPE: DNA
<213> ORGANISM: Artificial
<220> FEATURE:
<223> OTHER INFORMATION: Target sequence

<400> SEQUENCE: 13
agagtacatt tccacaaca                                               19

<210> SEQ ID NO 14
<211> LENGTH: 19
<212> TYPE: DNA
<213> ORGANISM: Artificial
<220> FEATURE:
<223> OTHER INFORMATION: Target sequence

<400> SEQUENCE: 14
acgatgaagg aacgagaaa                                               19

<210> SEQ ID NO 15
<211> LENGTH: 19
<212> TYPE: DNA
<213> ORGANISM: Artificial
<220> FEATURE:
<223> OTHER INFORMATION: Target sequence

<400> SEQUENCE: 15
atgcatagta acagcctga                                               19

<210> SEQ ID NO 16
<211> LENGTH: 19
<212> TYPE: DNA
<213> ORGANISM: Artificial
<220> FEATURE:
<223> OTHER INFORMATION: Target sequence

<400> SEQUENCE: 16
tgcatagtaa cagcctgaa                                               19

<210> SEQ ID NO 17
<211> LENGTH: 19
<212> TYPE: DNA
<213> ORGANISM: Artificial
<220> FEATURE:
<223> OTHER INFORMATION: Target sequence

<400> SEQUENCE: 17
```
atagtaacag cctgaacaa						19

<210> SEQ ID NO 18
<211> LENGTH: 19
<212> TYPE: DNA
<213> ORGANISM: Artificial
<220> FEATURE:
<223> OTHER INFORMATION: Target sequence

<400> SEQUENCE: 18
ggtgaagacc gatcaagaa						19

<210> SEQ ID NO 19
<211> LENGTH: 19
<212> TYPE: DNA
<213> ORGANISM: Artificial
<220> FEATURE:
<223> OTHER INFORMATION: Target sequence

<400> SEQUENCE: 19
tgaagaccga tcaagaaga						19

<210> SEQ ID NO 20
<211> LENGTH: 19
<212> TYPE: DNA
<213> ORGANISM: Artificial
<220> FEATURE:
<223> OTHER INFORMATION: Target sequence

<400> SEQUENCE: 20
tggacacgat ggtgacata						19

<210> SEQ ID NO 21
<211> LENGTH: 19
<212> TYPE: DNA
<213> ORGANISM: Artificial
<220> FEATURE:
<223> OTHER INFORMATION: Target sequence

<400> SEQUENCE: 21
gacacgatgg tgacataca						19

<210> SEQ ID NO 22
<211> LENGTH: 19
<212> TYPE: DNA
<213> ORGANISM: Artificial
<220> FEATURE:
<223> OTHER INFORMATION: Target sequence

<400> SEQUENCE: 22
acacgatggt gacatacat						19

<210> SEQ ID NO 23
<211> LENGTH: 19
<212> TYPE: DNA
<213> ORGANISM: Artificial
<220> FEATURE:
<223> OTHER INFORMATION: Target sequence

<400> SEQUENCE: 23
tgacgctgga ggatcacta						19

<210> SEQ ID NO 24
<211> LENGTH: 19
<212> TYPE: DNA
<213> ORGANISM: Artificial
<220> FEATURE:

```
<223> OTHER INFORMATION: Target sequence

<400> SEQUENCE: 24
gctgacgtgg cctaccata                                                    19

<210> SEQ ID NO 25
<211> LENGTH: 19
<212> TYPE: DNA
<213> ORGANISM: Artificial
<220> FEATURE:
<223> OTHER INFORMATION: Target sequence

<400> SEQUENCE: 25
ctgacgtggc ctaccataa                                                    19

<210> SEQ ID NO 26
<211> LENGTH: 19
<212> TYPE: DNA
<213> ORGANISM: Artificial
<220> FEATURE:
<223> OTHER INFORMATION: Target sequence

<400> SEQUENCE: 26
gacgtggcct accataaca                                                    19

<210> SEQ ID NO 27
<211> LENGTH: 19
<212> TYPE: DNA
<213> ORGANISM: Artificial
<220> FEATURE:
<223> OTHER INFORMATION: Target sequence

<400> SEQUENCE: 27
attcggagct ggcgctcat                                                    19

<210> SEQ ID NO 28
<211> LENGTH: 19
<212> TYPE: DNA
<213> ORGANISM: Artificial
<220> FEATURE:
<223> OTHER INFORMATION: Target sequence

<400> SEQUENCE: 28
agctggcgct catgtacaa                                                    19

<210> SEQ ID NO 29
<211> LENGTH: 19
<212> TYPE: DNA
<213> ORGANISM: Artificial
<220> FEATURE:
<223> OTHER INFORMATION: Target sequence

<400> SEQUENCE: 29
agtcggtgct cgagaatca                                                    19

<210> SEQ ID NO 30
<211> LENGTH: 19
<212> TYPE: DNA
<213> ORGANISM: Artificial
<220> FEATURE:
<223> OTHER INFORMATION: Target sequence

<400> SEQUENCE: 30
gaggacaact gcgacatct                                                    19

<210> SEQ ID NO 31
```

```
<211> LENGTH: 19
<212> TYPE: DNA
<213> ORGANISM: Artificial
<220> FEATURE:
<223> OTHER INFORMATION: Target sequence

<400> SEQUENCE: 31
ggcagagcct acgcaagat                                                    19

<210> SEQ ID NO 32
<211> LENGTH: 19
<212> TYPE: DNA
<213> ORGANISM: Artificial
<220> FEATURE:
<223> OTHER INFORMATION: Target sequence

<400> SEQUENCE: 32
tcctcctgct agataacta                                                    19

<210> SEQ ID NO 33
<211> LENGTH: 19
<212> TYPE: DNA
<213> ORGANISM: Artificial
<220> FEATURE:
<223> OTHER INFORMATION: Target sequence

<400> SEQUENCE: 33
tccaggtcct ccggaacat                                                    19

<210> SEQ ID NO 34
<211> LENGTH: 19
<212> TYPE: DNA
<213> ORGANISM: Artificial
<220> FEATURE:
<223> OTHER INFORMATION: Target sequence

<400> SEQUENCE: 34
gcgagcgtgg catggaaat                                                    19

<210> SEQ ID NO 35
<211> LENGTH: 19
<212> TYPE: DNA
<213> ORGANISM: Artificial
<220> FEATURE:
<223> OTHER INFORMATION: Target sequence

<400> SEQUENCE: 35
agctctggat gcaaccata                                                    19

<210> SEQ ID NO 36
<211> LENGTH: 19
<212> TYPE: DNA
<213> ORGANISM: Artificial
<220> FEATURE:
<223> OTHER INFORMATION: Target sequence

<400> SEQUENCE: 36
aggagtcgtt ggaagttat                                                    19

<210> SEQ ID NO 37
<211> LENGTH: 19
<212> TYPE: DNA
<213> ORGANISM: Artificial
<220> FEATURE:
<223> OTHER INFORMATION: Target sequence

<400> SEQUENCE: 37
```

| | |
|---|---|
| cgttggaagt tatggcaca | 19 |

<210> SEQ ID NO 38
<211> LENGTH: 19
<212> TYPE: DNA
<213> ORGANISM: Artificial
<220> FEATURE:
<223> OTHER INFORMATION: Target sequence

<400> SEQUENCE: 38

| | |
|---|---|
| tctagaacgt ggtcaggaa | 19 |

<210> SEQ ID NO 39
<211> LENGTH: 19
<212> TYPE: DNA
<213> ORGANISM: Artificial
<220> FEATURE:
<223> OTHER INFORMATION: Target sequence

<400> SEQUENCE: 39

| | |
|---|---|
| ctagaacgtg gtcaggaat | 19 |

<210> SEQ ID NO 40
<211> LENGTH: 19
<212> TYPE: DNA
<213> ORGANISM: Artificial
<220> FEATURE:
<223> OTHER INFORMATION: Target sequence

<400> SEQUENCE: 40

| | |
|---|---|
| tagaacgtgg tcaggaata | 19 |

<210> SEQ ID NO 41
<211> LENGTH: 19
<212> TYPE: DNA
<213> ORGANISM: Artificial
<220> FEATURE:
<223> OTHER INFORMATION: Target sequence

<400> SEQUENCE: 41

| | |
|---|---|
| agaacgtggt caggaatag | 19 |

<210> SEQ ID NO 42
<211> LENGTH: 19
<212> TYPE: DNA
<213> ORGANISM: Artificial
<220> FEATURE:
<223> OTHER INFORMATION: Target sequence

<400> SEQUENCE: 42

| | |
|---|---|
| ggtcaggaat agccattct | 19 |

<210> SEQ ID NO 43
<211> LENGTH: 19
<212> TYPE: DNA
<213> ORGANISM: Artificial
<220> FEATURE:
<223> OTHER INFORMATION: Target sequence

<400> SEQUENCE: 43

| | |
|---|---|
| aaagtcttcc gcttgattt | 19 |

<210> SEQ ID NO 44
<211> LENGTH: 19
<212> TYPE: DNA
<213> ORGANISM: Artificial
<220> FEATURE:

```
<223> OTHER INFORMATION: Target sequence

<400> SEQUENCE: 44
cgatactcct ggcgatact                                              19

<210> SEQ ID NO 45
<211> LENGTH: 19
<212> TYPE: DNA
<213> ORGANISM: Artificial
<220> FEATURE:
<223> OTHER INFORMATION: Target sequence

<400> SEQUENCE: 45
atactcctgg cgatactga                                              19

<210> SEQ ID NO 46
<211> LENGTH: 19
<212> TYPE: DNA
<213> ORGANISM: Artificial
<220> FEATURE:
<223> OTHER INFORMATION: Target sequence

<400> SEQUENCE: 46
ctggcgatac tgactagaa                                              19

<210> SEQ ID NO 47
<211> LENGTH: 19
<212> TYPE: DNA
<213> ORGANISM: Artificial
<220> FEATURE:
<223> OTHER INFORMATION: Target sequence

<400> SEQUENCE: 47
gcgatactga ctagaaagt                                              19

<210> SEQ ID NO 48
<211> LENGTH: 19
<212> TYPE: DNA
<213> ORGANISM: Artificial
<220> FEATURE:
<223> OTHER INFORMATION: Target sequence

<400> SEQUENCE: 48
cctaggagga agcaataat                                              19

<210> SEQ ID NO 49
<211> LENGTH: 19
<212> TYPE: DNA
<213> ORGANISM: Artificial
<220> FEATURE:
<223> OTHER INFORMATION: Target sequence

<400> SEQUENCE: 49
gaagcaataa tggtgtata                                              19

<210> SEQ ID NO 50
<211> LENGTH: 19
<212> TYPE: DNA
<213> ORGANISM: Artificial
<220> FEATURE:
<223> OTHER INFORMATION: Target sequence

<400> SEQUENCE: 50
tgtaaggttg gtttgtaaa                                              19

<210> SEQ ID NO 51
```

```
<211> LENGTH: 19
<212> TYPE: DNA
<213> ORGANISM: Artificial
<220> FEATURE:
<223> OTHER INFORMATION: Target sequence

<400> SEQUENCE: 51
gtaaggttgg tttgtaaat                                                  19

<210> SEQ ID NO 52
<211> LENGTH: 19
<212> TYPE: DNA
<213> ORGANISM: Artificial
<220> FEATURE:
<223> OTHER INFORMATION: Target sequence

<400> SEQUENCE: 52
cttgtgtatt gtccacttt                                                  19

<210> SEQ ID NO 53
<211> LENGTH: 19
<212> TYPE: DNA
<213> ORGANISM: Artificial
<220> FEATURE:
<223> OTHER INFORMATION: Target sequence

<400> SEQUENCE: 53
tgtgtattgt ccactttga                                                  19

<210> SEQ ID NO 54
<211> LENGTH: 19
<212> TYPE: DNA
<213> ORGANISM: Artificial
<220> FEATURE:
<223> OTHER INFORMATION: Target sequence

<400> SEQUENCE: 54
cagtcattcg gtccgttga                                                  19

<210> SEQ ID NO 55
<211> LENGTH: 19
<212> TYPE: DNA
<213> ORGANISM: Artificial
<220> FEATURE:
<223> OTHER INFORMATION: Target sequence

<400> SEQUENCE: 55
agtcattcgg tccgttgat                                                  19

<210> SEQ ID NO 56
<211> LENGTH: 19
<212> TYPE: DNA
<213> ORGANISM: Artificial
<220> FEATURE:
<223> OTHER INFORMATION: Target sequence

<400> SEQUENCE: 56
cattcggtcc gttgatcaa                                                  19

<210> SEQ ID NO 57
<211> LENGTH: 19
<212> TYPE: DNA
<213> ORGANISM: Artificial
<220> FEATURE:
<223> OTHER INFORMATION: Target sequence

<400> SEQUENCE: 57
```

-continued ttcggtccgt tgatcaata                                                19

<210> SEQ ID NO 58
<211> LENGTH: 19
<212> TYPE: DNA
<213> ORGANISM: Artificial
<220> FEATURE:
<223> OTHER INFORMATION: Target sequence

<400> SEQUENCE: 58
ttgatcaata atccttcga                                                19

<210> SEQ ID NO 59
<211> LENGTH: 19
<212> TYPE: DNA
<213> ORGANISM: Artificial
<220> FEATURE:
<223> OTHER INFORMATION: Target sequence

<400> SEQUENCE: 59
ccttcgatct tgtctccaa                                                19

<210> SEQ ID NO 60
<211> LENGTH: 19
<212> TYPE: DNA
<213> ORGANISM: Artificial
<220> FEATURE:
<223> OTHER INFORMATION: Target sequence

<400> SEQUENCE: 60
cttcgatctt gtctccaat                                                19

<210> SEQ ID NO 61
<211> LENGTH: 19
<212> TYPE: DNA
<213> ORGANISM: Artificial
<220> FEATURE:
<223> OTHER INFORMATION: Target sequence

<400> SEQUENCE: 61
gatcttgtct ccaattaaa                                                19

<210> SEQ ID NO 62
<211> LENGTH: 19
<212> TYPE: DNA
<213> ORGANISM: Artificial
<220> FEATURE:
<223> OTHER INFORMATION: Target sequence

<400> SEQUENCE: 62
gactatgact tgtcaccaa                                                19

<210> SEQ ID NO 63
<211> LENGTH: 19
<212> TYPE: DNA
<213> ORGANISM: Artificial
<220> FEATURE:
<223> OTHER INFORMATION: Target sequence

<400> SEQUENCE: 63
actatgactt gtcaccaaa                                                19

<210> SEQ ID NO 64
<211> LENGTH: 19
<212> TYPE: DNA
<213> ORGANISM: Artificial
<220> FEATURE:

```
<223> OTHER INFORMATION: Target sequence

<400> SEQUENCE: 64
acttcactat actgacaaa                                                      19

<210> SEQ ID NO 65
<211> LENGTH: 19
<212> TYPE: DNA
<213> ORGANISM: Artificial
<220> FEATURE:
<223> OTHER INFORMATION: Target sequence

<400> SEQUENCE: 65
accttcatgg tacatctaa                                                      19

<210> SEQ ID NO 66
<211> LENGTH: 19
<212> TYPE: DNA
<213> ORGANISM: Artificial
<220> FEATURE:
<223> OTHER INFORMATION: Target sequence

<400> SEQUENCE: 66
aaacgctgga ggaattaga                                                      19

<210> SEQ ID NO 67
<211> LENGTH: 19
<212> TYPE: DNA
<213> ORGANISM: Artificial
<220> FEATURE:
<223> OTHER INFORMATION: Target sequence

<400> SEQUENCE: 67
tcagtgagat ggcttctaa                                                      19

<210> SEQ ID NO 68
<211> LENGTH: 19
<212> TYPE: DNA
<213> ORGANISM: Artificial
<220> FEATURE:
<223> OTHER INFORMATION: Target sequence

<400> SEQUENCE: 68
atgcatagtt caagcctaa                                                      19

<210> SEQ ID NO 69
<211> LENGTH: 19
<212> TYPE: DNA
<213> ORGANISM: Artificial
<220> FEATURE:
<223> OTHER INFORMATION: Target sequence

<400> SEQUENCE: 69
tgcatcatgt atgctatat                                                      19

<210> SEQ ID NO 70
<211> LENGTH: 19
<212> TYPE: DNA
<213> ORGANISM: Artificial
<220> FEATURE:
<223> OTHER INFORMATION: Target sequence

<400> SEQUENCE: 70
ctacatgatg actttagaa                                                      19

<210> SEQ ID NO 71
```

```
<211> LENGTH: 19
<212> TYPE: DNA
<213> ORGANISM: Artificial
<220> FEATURE:
<223> OTHER INFORMATION: Target sequence

<400> SEQUENCE: 71
tgactttaga agaccatta                                                       19

<210> SEQ ID NO 72
<211> LENGTH: 19
<212> TYPE: DNA
<213> ORGANISM: Artificial
<220> FEATURE:
<223> OTHER INFORMATION: Target sequence

<400> SEQUENCE: 72
caggcgttct tctcctaga                                                       19

<210> SEQ ID NO 73
<211> LENGTH: 19
<212> TYPE: DNA
<213> ORGANISM: Artificial
<220> FEATURE:
<223> OTHER INFORMATION: Target sequence

<400> SEQUENCE: 73
cttctcctag acaactata                                                       19

<210> SEQ ID NO 74
<211> LENGTH: 19
<212> TYPE: DNA
<213> ORGANISM: Artificial
<220> FEATURE:
<223> OTHER INFORMATION: Target sequence

<400> SEQUENCE: 74
actataccga tcgcattca                                                       19

<210> SEQ ID NO 75
<211> LENGTH: 19
<212> TYPE: DNA
<213> ORGANISM: Artificial
<220> FEATURE:
<223> OTHER INFORMATION: Target sequence

<400> SEQUENCE: 75
gcattcaggt ccttcgcaa                                                       19

<210> SEQ ID NO 76
<211> LENGTH: 19
<212> TYPE: DNA
<213> ORGANISM: Artificial
<220> FEATURE:
<223> OTHER INFORMATION: Target sequence

<400> SEQUENCE: 76
attcaggtcc ttcgcaaca                                                       19

<210> SEQ ID NO 77
<211> LENGTH: 19
<212> TYPE: DNA
<213> ORGANISM: Artificial
<220> FEATURE:
<223> OTHER INFORMATION: Target sequence

<400> SEQUENCE: 77
```
ttcaggtcct tcgcaacat                                                19

<210> SEQ ID NO 78
<211> LENGTH: 19
<212> TYPE: DNA
<213> ORGANISM: Artificial
<220> FEATURE:
<223> OTHER INFORMATION: Target sequence

<400> SEQUENCE: 78
tccttcgcaa catggtaca                                                19

<210> SEQ ID NO 79
<211> LENGTH: 19
<212> TYPE: DNA
<213> ORGANISM: Artificial
<220> FEATURE:
<223> OTHER INFORMATION: Target sequence

<400> SEQUENCE: 79
ttggaattgt atcggcaat                                                19

<210> SEQ ID NO 80
<211> LENGTH: 19
<212> TYPE: DNA
<213> ORGANISM: Artificial
<220> FEATURE:
<223> OTHER INFORMATION: Target sequence

<400> SEQUENCE: 80
ctcgatacct tagaagata                                                19

<210> SEQ ID NO 81
<211> LENGTH: 19
<212> TYPE: DNA
<213> ORGANISM: Artificial
<220> FEATURE:
<223> OTHER INFORMATION: Target sequence

<400> SEQUENCE: 81
tcgatacctt agaagataa                                                19

<210> SEQ ID NO 82
<211> LENGTH: 19
<212> TYPE: DNA
<213> ORGANISM: Artificial
<220> FEATURE:
<223> OTHER INFORMATION: Target sequence

<400> SEQUENCE: 82
gagcatgata cctcaaagt                                                19

<210> SEQ ID NO 83
<211> LENGTH: 19
<212> TYPE: DNA
<213> ORGANISM: Artificial
<220> FEATURE:
<223> OTHER INFORMATION: Target sequence

<400> SEQUENCE: 83
ttgaactgac tctcgatga                                                19

<210> SEQ ID NO 84
<211> LENGTH: 19
<212> TYPE: DNA
<213> ORGANISM: Artificial
<220> FEATURE:

<223> OTHER INFORMATION: Target sequence

<400> SEQUENCE: 84
gattctgaag gacctgaga                                          19

<210> SEQ ID NO 85
<211> LENGTH: 19
<212> TYPE: DNA
<213> ORGANISM: Artificial
<220> FEATURE:
<223> OTHER INFORMATION: Target sequence

<400> SEQUENCE: 85
cgattctgat caagacaca                                          19

<210> SEQ ID NO 86
<211> LENGTH: 19
<212> TYPE: DNA
<213> ORGANISM: Artificial
<220> FEATURE:
<223> OTHER INFORMATION: Target sequence

<400> SEQUENCE: 86
agatcattct gcactaagt                                          19

<210> SEQ ID NO 87
<211> LENGTH: 19
<212> TYPE: DNA
<213> ORGANISM: Artificial
<220> FEATURE:
<223> OTHER INFORMATION: Target sequence

<400> SEQUENCE: 87
actgccttct gcgctaaca                                          19

<210> SEQ ID NO 88
<211> LENGTH: 19
<212> TYPE: DNA
<213> ORGANISM: Artificial
<220> FEATURE:
<223> OTHER INFORMATION: Target sequence

<400> SEQUENCE: 88
cacctccatt cctgtttat                                          19

<210> SEQ ID NO 89
<211> LENGTH: 19
<212> TYPE: DNA
<213> ORGANISM: Artificial
<220> FEATURE:
<223> OTHER INFORMATION: Target sequence

<400> SEQUENCE: 89
acctccattc ctgtttata                                          19

<210> SEQ ID NO 90
<211> LENGTH: 19
<212> TYPE: DNA
<213> ORGANISM: Artificial
<220> FEATURE:
<223> OTHER INFORMATION: Target sequence

<400> SEQUENCE: 90
atctaacatt gcctgccaa                                          19

<210> SEQ ID NO 91

```
<211> LENGTH: 19
<212> TYPE: DNA
<213> ORGANISM: Artificial
<220> FEATURE:
<223> OTHER INFORMATION: Target sequence

<400> SEQUENCE: 91
gtcacttagt agagacata                                                 19

<210> SEQ ID NO 92
<211> LENGTH: 19
<212> TYPE: DNA
<213> ORGANISM: Artificial
<220> FEATURE:
<223> OTHER INFORMATION: Target sequence

<400> SEQUENCE: 92
agttgctact tctgcacaa                                                 19

<210> SEQ ID NO 93
<211> LENGTH: 19
<212> TYPE: DNA
<213> ORGANISM: Artificial
<220> FEATURE:
<223> OTHER INFORMATION: Target sequence

<400> SEQUENCE: 93
ttataactgg atcctacta                                                 19

<210> SEQ ID NO 94
<211> LENGTH: 19
<212> TYPE: DNA
<213> ORGANISM: Artificial
<220> FEATURE:
<223> OTHER INFORMATION: Target sequence

<400> SEQUENCE: 94
tataactgga tcctactat                                                 19

<210> SEQ ID NO 95
<211> LENGTH: 19
<212> TYPE: DNA
<213> ORGANISM: Artificial
<220> FEATURE:
<223> OTHER INFORMATION: Target sequence

<400> SEQUENCE: 95
cactacattt gctcacaga                                                 19

<210> SEQ ID NO 96
<211> LENGTH: 19
<212> TYPE: DNA
<213> ORGANISM: Artificial
<220> FEATURE:
<223> OTHER INFORMATION: Target sequence

<400> SEQUENCE: 96
ccgaactact gactttgaa                                                 19

<210> SEQ ID NO 97
<211> LENGTH: 19
<212> TYPE: DNA
<213> ORGANISM: Artificial
<220> FEATURE:
<223> OTHER INFORMATION: Target sequence

<400> SEQUENCE: 97
```

-continued gtcatgttcc agttcatta                                            19

<210> SEQ ID NO 98
<211> LENGTH: 19
<212> TYPE: DNA
<213> ORGANISM: Artificial
<220> FEATURE:
<223> OTHER INFORMATION: Target sequence

<400> SEQUENCE: 98
tgtagcaaat tacgcaaat                                            19

<210> SEQ ID NO 99
<211> LENGTH: 19
<212> TYPE: DNA
<213> ORGANISM: Artificial
<220> FEATURE:
<223> OTHER INFORMATION: Target sequence

<400> SEQUENCE: 99
gtagcaaatt acgcaaatg                                            19

<210> SEQ ID NO 100
<211> LENGTH: 19
<212> TYPE: DNA
<213> ORGANISM: Artificial
<220> FEATURE:
<223> OTHER INFORMATION: Target sequence

<400> SEQUENCE: 100
acgcaaatgt gaagcctct                                            19

<210> SEQ ID NO 101
<211> LENGTH: 19
<212> TYPE: DNA
<213> ORGANISM: Artificial
<220> FEATURE:
<223> OTHER INFORMATION: Target sequence

<400> SEQUENCE: 101
gtttcatgct ttcagttca                                            19

<210> SEQ ID NO 102
<211> LENGTH: 19
<212> TYPE: DNA
<213> ORGANISM: Artificial
<220> FEATURE:
<223> OTHER INFORMATION: Target sequence

<400> SEQUENCE: 102
agttcagcat tgtgactca                                            19

<210> SEQ ID NO 103
<211> LENGTH: 19
<212> TYPE: DNA
<213> ORGANISM: Artificial
<220> FEATURE:
<223> OTHER INFORMATION: Target sequence

<400> SEQUENCE: 103
cagcattgtg actcagtaa                                            19

<210> SEQ ID NO 104
<211> LENGTH: 19
<212> TYPE: DNA
<213> ORGANISM: Artificial
<220> FEATURE:

<223> OTHER INFORMATION: Target sequence

<400> SEQUENCE: 104
agcattgtga ctcagtaat                                                19

<210> SEQ ID NO 105
<211> LENGTH: 19
<212> TYPE: DNA
<213> ORGANISM: Artificial
<220> FEATURE:
<223> OTHER INFORMATION: Target sequence

<400> SEQUENCE: 105
catgaccaat gtatgtcta                                                19

<210> SEQ ID NO 106
<211> LENGTH: 19
<212> TYPE: DNA
<213> ORGANISM: Artificial
<220> FEATURE:
<223> OTHER INFORMATION: Target sequence

<400> SEQUENCE: 106
atgaccaatg tatgtctat                                                19

<210> SEQ ID NO 107
<211> LENGTH: 19
<212> TYPE: DNA
<213> ORGANISM: Artificial
<220> FEATURE:
<223> OTHER INFORMATION: Target sequence

<400> SEQUENCE: 107
cattgtttca ggtggacat                                                19

<210> SEQ ID NO 108
<211> LENGTH: 19
<212> TYPE: DNA
<213> ORGANISM: Artificial
<220> FEATURE:
<223> OTHER INFORMATION: Target sequence

<400> SEQUENCE: 108
tctattcgga tccggacaa                                                19

<210> SEQ ID NO 109
<211> LENGTH: 19
<212> TYPE: DNA
<213> ORGANISM: Artificial
<220> FEATURE:
<223> OTHER INFORMATION: Target sequence

<400> SEQUENCE: 109
ttcctgtacc gctcagata                                                19

<210> SEQ ID NO 110
<211> LENGTH: 19
<212> TYPE: DNA
<213> ORGANISM: Artificial
<220> FEATURE:
<223> OTHER INFORMATION: Target sequence

<400> SEQUENCE: 110
ccgctcagat agcgactat                                                19

<210> SEQ ID NO 111

```
<211> LENGTH: 19
<212> TYPE: DNA
<213> ORGANISM: Artificial
<220> FEATURE:
<223> OTHER INFORMATION: Target sequence

<400> SEQUENCE: 111
ggagaggaca tgattgtga                                            19

<210> SEQ ID NO 112
<211> LENGTH: 19
<212> TYPE: DNA
<213> ORGANISM: Artificial
<220> FEATURE:
<223> OTHER INFORMATION: Target sequence

<400> SEQUENCE: 112
tggcattgga gacgctaga                                            19

<210> SEQ ID NO 113
<211> LENGTH: 19
<212> TYPE: DNA
<213> ORGANISM: Artificial
<220> FEATURE:
<223> OTHER INFORMATION: Target sequence

<400> SEQUENCE: 113
ccaacaagtt caagcggat                                            19

<210> SEQ ID NO 114
<211> LENGTH: 19
<212> TYPE: DNA
<213> ORGANISM: Artificial
<220> FEATURE:
<223> OTHER INFORMATION: Target sequence

<400> SEQUENCE: 114
agttcaagcg gatcctgaa                                            19

<210> SEQ ID NO 115
<211> LENGTH: 19
<212> TYPE: DNA
<213> ORGANISM: Artificial
<220> FEATURE:
<223> OTHER INFORMATION: Target sequence

<400> SEQUENCE: 115
ccggatcagt ggcctacat                                            19

<210> SEQ ID NO 116
<211> LENGTH: 19
<212> TYPE: DNA
<213> ORGANISM: Artificial
<220> FEATURE:
<223> OTHER INFORMATION: Target sequence

<400> SEQUENCE: 116
ctcacagcta tcatattca                                            19

<210> SEQ ID NO 117
<211> LENGTH: 19
<212> TYPE: DNA
<213> ORGANISM: Artificial
<220> FEATURE:
<223> OTHER INFORMATION: Target sequence

<400> SEQUENCE: 117
```
gtcactacca cgccaatgt                                        19

<210> SEQ ID NO 118
<211> LENGTH: 19
<212> TYPE: DNA
<213> ORGANISM: Artificial
<220> FEATURE:
<223> OTHER INFORMATION: Target sequence

<400> SEQUENCE: 118
acgcatgtgc tgctggcta                                        19

<210> SEQ ID NO 119
<211> LENGTH: 19
<212> TYPE: DNA
<213> ORGANISM: Artificial
<220> FEATURE:
<223> OTHER INFORMATION: Target sequence

<400> SEQUENCE: 119
ttgcaagcgc catccacga                                        19

<210> SEQ ID NO 120
<211> LENGTH: 19
<212> TYPE: DNA
<213> ORGANISM: Artificial
<220> FEATURE:
<223> OTHER INFORMATION: Target sequence

<400> SEQUENCE: 120
actcagacgt ggcgcttat                                        19

<210> SEQ ID NO 121
<211> LENGTH: 19
<212> TYPE: DNA
<213> ORGANISM: Artificial
<220> FEATURE:
<223> OTHER INFORMATION: Target sequence

<400> SEQUENCE: 121
tcagacgtgg cgcttatgt                                        19

<210> SEQ ID NO 122
<211> LENGTH: 19
<212> TYPE: DNA
<213> ORGANISM: Artificial
<220> FEATURE:
<223> OTHER INFORMATION: Target sequence

<400> SEQUENCE: 122
cagacgtggc gcttatgta                                        19

<210> SEQ ID NO 123
<211> LENGTH: 19
<212> TYPE: DNA
<213> ORGANISM: Artificial
<220> FEATURE:
<223> OTHER INFORMATION: Target sequence

<400> SEQUENCE: 123
acgtggcgct tatgtacaa                                        19

<210> SEQ ID NO 124
<211> LENGTH: 19
<212> TYPE: DNA
<213> ORGANISM: Artificial
<220> FEATURE:

<223> OTHER INFORMATION: Target sequence

<400> SEQUENCE: 124
acatgaacct cctggccga                                                    19

<210> SEQ ID NO 125
<211> LENGTH: 19
<212> TYPE: DNA
<213> ORGANISM: Artificial
<220> FEATURE:
<223> OTHER INFORMATION: Target sequence

<400> SEQUENCE: 125
ggacaactat tccgaccga                                                    19

<210> SEQ ID NO 126
<211> LENGTH: 19
<212> TYPE: DNA
<213> ORGANISM: Artificial
<220> FEATURE:
<223> OTHER INFORMATION: Target sequence

<400> SEQUENCE: 126
gacaactatt ccgaccgaa                                                    19

<210> SEQ ID NO 127
<211> LENGTH: 19
<212> TYPE: DNA
<213> ORGANISM: Artificial
<220> FEATURE:
<223> OTHER INFORMATION: Target sequence

<400> SEQUENCE: 127
acaactattc cgaccgaat                                                    19

<210> SEQ ID NO 128
<211> LENGTH: 19
<212> TYPE: DNA
<213> ORGANISM: Artificial
<220> FEATURE:
<223> OTHER INFORMATION: Target sequence

<400> SEQUENCE: 128
gaatccaggt cttgcagaa                                                    19

<210> SEQ ID NO 129
<211> LENGTH: 19
<212> TYPE: DNA
<213> ORGANISM: Artificial
<220> FEATURE:
<223> OTHER INFORMATION: Target sequence

<400> SEQUENCE: 129
tgacaagcat acggcctca                                                    19

<210> SEQ ID NO 130
<211> LENGTH: 19
<212> TYPE: DNA
<213> ORGANISM: Artificial
<220> FEATURE:
<223> OTHER INFORMATION: Target sequence

<400> SEQUENCE: 130
acaagcatac ggcctcagt                                                    19

<210> SEQ ID NO 131

```
<211> LENGTH: 19
<212> TYPE: DNA
<213> ORGANISM: Artificial
<220> FEATURE:
<223> OTHER INFORMATION: Target sequence

<400> SEQUENCE: 131
ctgacagatt ccagtttga                                                        19

<210> SEQ ID NO 132
<211> LENGTH: 19
<212> TYPE: DNA
<213> ORGANISM: Artificial
<220> FEATURE:
<223> OTHER INFORMATION: Target sequence

<400> SEQUENCE: 132
agagacagct ttagccaaa                                                        19

<210> SEQ ID NO 133
<211> LENGTH: 19
<212> TYPE: DNA
<213> ORGANISM: Artificial
<220> FEATURE:
<223> OTHER INFORMATION: Target sequence

<400> SEQUENCE: 133
agacagcttt agccaaaga                                                        19

<210> SEQ ID NO 134
<211> LENGTH: 19
<212> TYPE: DNA
<213> ORGANISM: Artificial
<220> FEATURE:
<223> OTHER INFORMATION: Target sequence

<400> SEQUENCE: 134
gccttggagt tgcctgaca                                                        19

<210> SEQ ID NO 135
<211> LENGTH: 19
<212> TYPE: DNA
<213> ORGANISM: Artificial
<220> FEATURE:
<223> OTHER INFORMATION: Target sequence

<400> SEQUENCE: 135
tcgacaacca gaggactta                                                        19

<210> SEQ ID NO 136
<211> LENGTH: 19
<212> TYPE: DNA
<213> ORGANISM: Artificial
<220> FEATURE:
<223> OTHER INFORMATION: Target sequence

<400> SEQUENCE: 136
caatcaagct cttagttat                                                        19

<210> SEQ ID NO 137
<211> LENGTH: 19
<212> TYPE: DNA
<213> ORGANISM: Artificial
<220> FEATURE:
<223> OTHER INFORMATION: Target sequence

<400> SEQUENCE: 137
```
cctctccagt ggtcactct                                          19

<210> SEQ ID NO 138
<211> LENGTH: 19
<212> TYPE: DNA
<213> ORGANISM: Artificial
<220> FEATURE:
<223> OTHER INFORMATION: Target sequence

<400> SEQUENCE: 138
ggtcactctt gagtcacat                                          19

<210> SEQ ID NO 139
<211> LENGTH: 19
<212> TYPE: DNA
<213> ORGANISM: Artificial
<220> FEATURE:
<223> OTHER INFORMATION: Target sequence

<400> SEQUENCE: 139
gtcacatctg tcacttaat                                          19

<210> SEQ ID NO 140
<211> LENGTH: 19
<212> TYPE: DNA
<213> ORGANISM: Artificial
<220> FEATURE:
<223> OTHER INFORMATION: Target sequence

<400> SEQUENCE: 140
agcaccaaag cttcactca                                          19

<210> SEQ ID NO 141
<211> LENGTH: 19
<212> TYPE: DNA
<213> ORGANISM: Artificial
<220> FEATURE:
<223> OTHER INFORMATION: Target sequence

<400> SEQUENCE: 141
gcaccaaagc ttcactcat                                          19

<210> SEQ ID NO 142
<211> LENGTH: 19
<212> TYPE: DNA
<213> ORGANISM: Artificial
<220> FEATURE:
<223> OTHER INFORMATION: Target sequence

<400> SEQUENCE: 142
caccaaagct tcactcata                                          19

<210> SEQ ID NO 143
<211> LENGTH: 19
<212> TYPE: DNA
<213> ORGANISM: Artificial
<220> FEATURE:
<223> OTHER INFORMATION: Target sequence

<400> SEQUENCE: 143
ggcaaggcat agtggctta                                          19

<210> SEQ ID NO 144
<211> LENGTH: 19
<212> TYPE: DNA
<213> ORGANISM: Artificial
<220> FEATURE:

<223> OTHER INFORMATION: Target sequence

<400> SEQUENCE: 144
ggctaattct ccaagcaaa                                                      19

<210> SEQ ID NO 145
<211> LENGTH: 19
<212> TYPE: DNA
<213> ORGANISM: Artificial
<220> FEATURE:
<223> OTHER INFORMATION: Target sequence

<400> SEQUENCE: 145
tcgatccgac agcgattat                                                      19

<210> SEQ ID NO 146
<211> LENGTH: 19
<212> TYPE: DNA
<213> ORGANISM: Artificial
<220> FEATURE:
<223> OTHER INFORMATION: Target sequence

<400> SEQUENCE: 146
attatgacct ctctccaaa                                                      19

<210> SEQ ID NO 147
<211> LENGTH: 19
<212> TYPE: DNA
<213> ORGANISM: Artificial
<220> FEATURE:
<223> OTHER INFORMATION: Target sequence

<400> SEQUENCE: 147
ctccattgcc agtgatata                                                      19

<210> SEQ ID NO 148
<211> LENGTH: 19
<212> TYPE: DNA
<213> ORGANISM: Artificial
<220> FEATURE:
<223> OTHER INFORMATION: Target sequence

<400> SEQUENCE: 148
ggagatgact tgattgtga                                                      19

<210> SEQ ID NO 149
<211> LENGTH: 19
<212> TYPE: DNA
<213> ORGANISM: Artificial
<220> FEATURE:
<223> OTHER INFORMATION: Target sequence

<400> SEQUENCE: 149
ctgcgaactg tacgaaaca                                                      19

<210> SEQ ID NO 150
<211> LENGTH: 19
<212> TYPE: DNA
<213> ORGANISM: Artificial
<220> FEATURE:
<223> OTHER INFORMATION: Target sequence

<400> SEQUENCE: 150
tgcgaactgt acgaaacaa                                                      19

<210> SEQ ID NO 151

```
<211> LENGTH: 19
<212> TYPE: DNA
<213> ORGANISM: Artificial
<220> FEATURE:
<223> OTHER INFORMATION: Target sequence

<400> SEQUENCE: 151
gagtcggtct ggaaatcaa                                                  19

<210> SEQ ID NO 152
<211> LENGTH: 19
<212> TYPE: DNA
<213> ORGANISM: Artificial
<220> FEATURE:
<223> OTHER INFORMATION: Target sequence

<400> SEQUENCE: 152
tgactctcga agaccatta                                                  19

<210> SEQ ID NO 153
<211> LENGTH: 19
<212> TYPE: DNA
<213> ORGANISM: Artificial
<220> FEATURE:
<223> OTHER INFORMATION: Target sequence

<400> SEQUENCE: 153
atgctgatgt ggcctatca                                                  19

<210> SEQ ID NO 154
<211> LENGTH: 19
<212> TYPE: DNA
<213> ORGANISM: Artificial
<220> FEATURE:
<223> OTHER INFORMATION: Target sequence

<400> SEQUENCE: 154
gtctactcat gtgctatta                                                  19

<210> SEQ ID NO 155
<211> LENGTH: 19
<212> TYPE: DNA
<213> ORGANISM: Artificial
<220> FEATURE:
<223> OTHER INFORMATION: Target sequence

<400> SEQUENCE: 155
tgcaatacat gatgtagat                                                  19

<210> SEQ ID NO 156
<211> LENGTH: 19
<212> TYPE: DNA
<213> ORGANISM: Artificial
<220> FEATURE:
<223> OTHER INFORMATION: Target sequence

<400> SEQUENCE: 156
ttgccttgat gtacaatga                                                  19

<210> SEQ ID NO 157
<211> LENGTH: 19
<212> TYPE: DNA
<213> ORGANISM: Artificial
<220> FEATURE:
<223> OTHER INFORMATION: Target sequence

<400> SEQUENCE: 157
```

```
atgattcctc agtcttaga                                                19
```

<210> SEQ ID NO 158
<211> LENGTH: 19
<212> TYPE: DNA
<213> ORGANISM: Artificial
<220> FEATURE:
<223> OTHER INFORMATION: Target sequence

<400> SEQUENCE: 158

```
acatcgtact tgcaacaga                                                19
```

<210> SEQ ID NO 159
<211> LENGTH: 19
<212> TYPE: DNA
<213> ORGANISM: Artificial
<220> FEATURE:
<223> OTHER INFORMATION: Target sequence

<400> SEQUENCE: 159

```
acatgaatct actggctga                                                19
```

<210> SEQ ID NO 160
<211> LENGTH: 19
<212> TYPE: DNA
<213> ORGANISM: Artificial
<220> FEATURE:
<223> OTHER INFORMATION: Target sequence

<400> SEQUENCE: 160

```
agactatggt tgaaactaa                                                19
```

<210> SEQ ID NO 161
<211> LENGTH: 19
<212> TYPE: DNA
<213> ORGANISM: Artificial
<220> FEATURE:
<223> OTHER INFORMATION: Target sequence

<400> SEQUENCE: 161

```
ctatggttga aactaagaa                                                19
```

<210> SEQ ID NO 162
<211> LENGTH: 19
<212> TYPE: DNA
<213> ORGANISM: Artificial
<220> FEATURE:
<223> OTHER INFORMATION: Target sequence

<400> SEQUENCE: 162

```
ccgataggat tcaggttct                                                19
```

<210> SEQ ID NO 163
<211> LENGTH: 19
<212> TYPE: DNA
<213> ORGANISM: Artificial
<220> FEATURE:
<223> OTHER INFORMATION: Target sequence

<400> SEQUENCE: 163

```
cagtggacgg accggataa                                                19
```

<210> SEQ ID NO 164
<211> LENGTH: 19
<212> TYPE: DNA
<213> ORGANISM: Artificial
<220> FEATURE:

```
<223> OTHER INFORMATION: Target sequence

<400> SEQUENCE: 164
ggaacgtggc atggagata                                              19

<210> SEQ ID NO 165
<211> LENGTH: 19
<212> TYPE: DNA
<213> ORGANISM: Artificial
<220> FEATURE:
<223> OTHER INFORMATION: Target sequence

<400> SEQUENCE: 165
gaacgtggca tggagataa                                              19

<210> SEQ ID NO 166
<211> LENGTH: 19
<212> TYPE: DNA
<213> ORGANISM: Artificial
<220> FEATURE:
<223> OTHER INFORMATION: Target sequence

<400> SEQUENCE: 166
gaatggtacc agagcacaa                                              19

<210> SEQ ID NO 167
<211> LENGTH: 19
<212> TYPE: DNA
<213> ORGANISM: Artificial
<220> FEATURE:
<223> OTHER INFORMATION: Target sequence

<400> SEQUENCE: 167
tgaactaact ttagaggaa                                              19

<210> SEQ ID NO 168
<211> LENGTH: 19
<212> TYPE: DNA
<213> ORGANISM: Artificial
<220> FEATURE:
<223> OTHER INFORMATION: Target sequence

<400> SEQUENCE: 168
cagtggcagt caagtggaa                                              19

<210> SEQ ID NO 169
<211> LENGTH: 19
<212> TYPE: DNA
<213> ORGANISM: Artificial
<220> FEATURE:
<223> OTHER INFORMATION: Target sequence

<400> SEQUENCE: 169
gactcagagt ctactgaaa                                              19

<210> SEQ ID NO 170
<211> LENGTH: 19
<212> TYPE: DNA
<213> ORGANISM: Artificial
<220> FEATURE:
<223> OTHER INFORMATION: Target sequence

<400> SEQUENCE: 170
tgtcatagat gatcgttct                                              19

<210> SEQ ID NO 171
```

-continued

```
<211> LENGTH: 19
<212> TYPE: DNA
<213> ORGANISM: Artificial
<220> FEATURE:
<223> OTHER INFORMATION: Target sequence

<400> SEQUENCE: 171
atggacgaag caacaaata                                                    19

<210> SEQ ID NO 172
<211> LENGTH: 19
<212> TYPE: DNA
<213> ORGANISM: Artificial
<220> FEATURE:
<223> OTHER INFORMATION: Target sequence

<400> SEQUENCE: 172
cctgatacat gactgaata                                                    19

<210> SEQ ID NO 173
<211> LENGTH: 19
<212> TYPE: DNA
<213> ORGANISM: Artificial
<220> FEATURE:
<223> OTHER INFORMATION: Target sequence

<400> SEQUENCE: 173
cctacttagt atctcctaa                                                    19

<210> SEQ ID NO 174
<211> LENGTH: 19
<212> TYPE: DNA
<213> ORGANISM: Artificial
<220> FEATURE:
<223> OTHER INFORMATION: Target sequence

<400> SEQUENCE: 174
agtgcatgtc tttctaata                                                    19

<210> SEQ ID NO 175
<211> LENGTH: 19
<212> TYPE: DNA
<213> ORGANISM: Artificial
<220> FEATURE:
<223> OTHER INFORMATION: Target sequence

<400> SEQUENCE: 175
tagatgaggt cttgtcaaa                                                    19

<210> SEQ ID NO 176
<211> LENGTH: 19
<212> TYPE: DNA
<213> ORGANISM: Artificial
<220> FEATURE:
<223> OTHER INFORMATION: Target sequence

<400> SEQUENCE: 176
tgaggtcttg tcaaatata                                                    19

<210> SEQ ID NO 177
<211> LENGTH: 19
<212> TYPE: DNA
<213> ORGANISM: Artificial
<220> FEATURE:
<223> OTHER INFORMATION: Target sequence

<400> SEQUENCE: 177
```

-continued gaggtcttgt caaatatat 19

<210> SEQ ID NO 178
<211> LENGTH: 19
<212> TYPE: DNA
<213> ORGANISM: Artificial
<220> FEATURE:
<223> OTHER INFORMATION: Target sequence

<400> SEQUENCE: 178
accacgaggt tgtatatca 19

<210> SEQ ID NO 179
<211> LENGTH: 19
<212> TYPE: DNA
<213> ORGANISM: Artificial
<220> FEATURE:
<223> OTHER INFORMATION: Target sequence

<400> SEQUENCE: 179
ccacgaggtt gtatatcat 19

<210> SEQ ID NO 180
<211> LENGTH: 19
<212> TYPE: DNA
<213> ORGANISM: Artificial
<220> FEATURE:
<223> OTHER INFORMATION: Target sequence

<400> SEQUENCE: 180
agaaacggct ttaagtgta 19

<210> SEQ ID NO 181
<211> LENGTH: 19
<212> TYPE: DNA
<213> ORGANISM: Artificial
<220> FEATURE:
<223> OTHER INFORMATION: Target sequence

<400> SEQUENCE: 181
ttaatggaca gccacataa 19

<210> SEQ ID NO 182
<211> LENGTH: 19
<212> TYPE: DNA
<213> ORGANISM: Artificial
<220> FEATURE:
<223> OTHER INFORMATION: Target sequence

<400> SEQUENCE: 182
gcaaatgact catgctgaa 19

<210> SEQ ID NO 183
<211> LENGTH: 19
<212> TYPE: DNA
<213> ORGANISM: Artificial
<220> FEATURE:
<223> OTHER INFORMATION: Target sequence

<400> SEQUENCE: 183
acgtatgttt gaccaagta 19

<210> SEQ ID NO 184
<211> LENGTH: 19
<212> TYPE: DNA
<213> ORGANISM: Artificial

```
<220> FEATURE:
<223> OTHER INFORMATION: Target sequence

<400> SEQUENCE: 184
ccaagtagtt tcacaagaa                                                19

<210> SEQ ID NO 185
<211> LENGTH: 19
<212> TYPE: DNA
<213> ORGANISM: Artificial
<220> FEATURE:
<223> OTHER INFORMATION: Target sequence

<400> SEQUENCE: 185
caagtagttt cacaagaat                                                19

<210> SEQ ID NO 186
<211> LENGTH: 19
<212> TYPE: DNA
<213> ORGANISM: Artificial
<220> FEATURE:
<223> OTHER INFORMATION: Target sequence

<400> SEQUENCE: 186
tgagtgaagt ctagaaaga                                                19

<210> SEQ ID NO 187
<211> LENGTH: 19
<212> TYPE: DNA
<213> ORGANISM: Artificial
<220> FEATURE:
<223> OTHER INFORMATION: Target sequence

<400> SEQUENCE: 187
ggactaatgc actgtacaa                                                19

<210> SEQ ID NO 188
<211> LENGTH: 19
<212> TYPE: DNA
<213> ORGANISM: Artificial
<220> FEATURE:
<223> OTHER INFORMATION: Target sequence

<400> SEQUENCE: 188
tggctttaca tttcctaaa                                                19

<210> SEQ ID NO 189
<211> LENGTH: 19
<212> TYPE: DNA
<213> ORGANISM: Artificial
<220> FEATURE:
<223> OTHER INFORMATION: Target sequence

<400> SEQUENCE: 189
catttcagct tgcaagtta                                                19

<210> SEQ ID NO 190
<211> LENGTH: 19
<212> TYPE: DNA
<213> ORGANISM: Artificial
<220> FEATURE:
<223> OTHER INFORMATION: Target sequence

<400> SEQUENCE: 190
gtctgtttac aaccatgta                                                19
```

```
<210> SEQ ID NO 191
<211> LENGTH: 19
<212> TYPE: DNA
<213> ORGANISM: Artificial
<220> FEATURE:
<223> OTHER INFORMATION: Target sequence

<400> SEQUENCE: 191
tgaatggtgt gtatacata                                               19

<210> SEQ ID NO 192
<211> LENGTH: 19
<212> TYPE: DNA
<213> ORGANISM: Artificial
<220> FEATURE:
<223> OTHER INFORMATION: Target sequence

<400> SEQUENCE: 192
atatagtctt gtcacctta                                               19

<210> SEQ ID NO 193
<211> LENGTH: 19
<212> TYPE: DNA
<213> ORGANISM: Artificial
<220> FEATURE:
<223> OTHER INFORMATION: Target sequence

<400> SEQUENCE: 193
atagtcttgt caccttaga                                               19

<210> SEQ ID NO 194
<211> LENGTH: 19
<212> TYPE: DNA
<213> ORGANISM: Artificial
<220> FEATURE:
<223> OTHER INFORMATION: Target sequence

<400> SEQUENCE: 194
caccttagag cttgtttat                                               19

<210> SEQ ID NO 195
<211> LENGTH: 19
<212> TYPE: DNA
<213> ORGANISM: Artificial
<220> FEATURE:
<223> OTHER INFORMATION: Target sequence

<400> SEQUENCE: 195
ggctgtgcct taactttaa                                               19

<210> SEQ ID NO 196
<211> LENGTH: 19
<212> TYPE: DNA
<213> ORGANISM: Artificial
<220> FEATURE:
<223> OTHER INFORMATION: Target sequence

<400> SEQUENCE: 196
gccttaactt taaccaata                                               19

<210> SEQ ID NO 197
<211> LENGTH: 19
<212> TYPE: DNA
<213> ORGANISM: Artificial
<220> FEATURE:
<223> OTHER INFORMATION: Target sequence
```

-continued

<400> SEQUENCE: 197
gattagaatt ctgccaata                                                    19

<210> SEQ ID NO 198
<211> LENGTH: 19
<212> TYPE: DNA
<213> ORGANISM: Artificial
<220> FEATURE:
<223> OTHER INFORMATION: Target sequence

<400> SEQUENCE: 198
atctgttgat caggaacta                                                    19

<210> SEQ ID NO 199
<211> LENGTH: 19
<212> TYPE: DNA
<213> ORGANISM: Artificial
<220> FEATURE:
<223> OTHER INFORMATION: Target sequence

<400> SEQUENCE: 199
aggaactact tcagctact                                                    19

<210> SEQ ID NO 200
<211> LENGTH: 19
<212> TYPE: RNA
<213> ORGANISM: Artificial
<220> FEATURE:
<223> OTHER INFORMATION: Sense strand

<400> SEQUENCE: 200
aaaggauguu gaaccguga                                                    19

<210> SEQ ID NO 201
<211> LENGTH: 19
<212> TYPE: RNA
<213> ORGANISM: Artificial
<220> FEATURE:
<223> OTHER INFORMATION: Antisense strand

<400> SEQUENCE: 201
ucacgguuca acauccuuu                                                    19

<210> SEQ ID NO 202
<211> LENGTH: 25
<212> TYPE: DNA
<213> ORGANISM: Artificial
<220> FEATURE:
<223> OTHER INFORMATION: Sense strand

<400> SEQUENCE: 202
aaaggatgtt gaaccgtgag ctcac                                             25

<210> SEQ ID NO 203
<211> LENGTH: 25
<212> TYPE: RNA
<213> ORGANISM: Artificial
<220> FEATURE:
<223> OTHER INFORMATION: Sense strand

<400> SEQUENCE: 203
aaaggauguu gaaccgugag cucac                                             25

```
<210> SEQ ID NO 204
<211> LENGTH: 27
<212> TYPE: RNA
<213> ORGANISM: Artificial
<220> FEATURE:
<223> OTHER INFORMATION: Antisense strand

<400> SEQUENCE: 204
gugagcucac gguucaacau ccuuuuu                                          27

<210> SEQ ID NO 205
<211> LENGTH: 19
<212> TYPE: DNA
<213> ORGANISM: Artificial
<220> FEATURE:
<223> OTHER INFORMATION: Target sequence

<400> SEQUENCE: 205
gaaatcaagt gtcagagtt                                                   19

<210> SEQ ID NO 206
<211> LENGTH: 19
<212> TYPE: DNA
<213> ORGANISM: Artificial
<220> FEATURE:
<223> OTHER INFORMATION: Target sequence

<400> SEQUENCE: 206
gaacttgcct tgatgtaca                                                   19

<210> SEQ ID NO 207
<211> LENGTH: 19
<212> TYPE: DNA
<213> ORGANISM: Artificial
<220> FEATURE:
<223> OTHER INFORMATION: Target sequence

<400> SEQUENCE: 207
ccaaggaact agaagatgt                                                   19
```

RNAI-MEDIATED INHIBITION OF PHOSPHODIESTERASE TYPE 4 FOR TREATMENT OF CAMP-RELATED OCULAR DISORDERS

The present application is a continuation of U.S. patent application Ser. No. 11/617,604 filed Dec. 28, 2006, which claims benefit to Provisional Application Ser. No. 60/754,372 filed Dec. 28, 2005, the text of which is specifically incorporated by reference herein.

FIELD OF THE INVENTION

The present invention relates to the field of interfering RNA compositions for inhibition of function of phosphodiesterase type 4 in cyclic AMP-related ocular disorders, particularly for treatment of dry eye, inflammation, and conjunctivitis.

BACKGROUND OF THE INVENTION

Dry eye, also known as conjunctivitis sicca or keratoconjunctivitis sicca, is a common ophthalmological disorder involving breakdown of the pre-ocular tear film, resulting in dehydration of the exposed outer surface of the eye.

Atopic keratoconjunctivitis involves inflammation of the conjunctiva and cornea characterized by intensely itchy red areas on the eyelids, a discharge, or scaly and crusty eyelids. The eyes may become sensitive to light and the eyelids may noticeably thicken. Permanent scarring of the cornea may occur due to rubbing and scratching of the eyes resulting in visual changes.

Vernal keratoconjunctivitis can occur under dry, dusty, windy, and warm weather conditions. Eyes can become intensely itchy, sensitive to light, and can produce a stringy discharge; eyelids may feel uncomfortable and droopy. An examination of the eye reveals severe inflammation due to a vast number of mast cells and accumulated eosinophils.

In giant papillary conjunctivitis, large papillae, or bumps, develop on the conjunctiva under the upper eyelid. Redness and itching of the eye develop along with a thick discharge due to irritation from a foreign substance.

To date, dry eye has been treated with topical administration of artificial tear solutions. Some of these solutions contain mucomimetic substances to temporarily replace or replenish the mucin layer in mucin deficient patients. Use of methylprednisolone has been proposed in a short-term "pulse" treatment to treat exacerbations of dry eye. The proposed "pulse" therapy is required to avoid complications associated with traditional steroid therapy for inflammatory conditions such as increased intraocular pressure and cataract formation.

Inflammation is generally treated with a standard anti-inflammatory regimen that includes steroids and/or non-steroidal anti-inflammatory drugs. These classes of drugs have potential side effects including intraocular pressure increase, cataract, glaucoma or corneal melting.

Vernal keratoconjunctivitis, giant papillary conjunctivitis and atopic keratoconjunctivitis have historically been treated with a regimen of oral or topical antihistamine and/or oral or topical steroid. Systemic treatment typically requires higher concentrations of the drug compound to be administered to afford an effective concentration to reach the necessary treatment site. Antihistamine compounds are known to have CNS activity, which manifest in drowsiness and drying of mucus membranes. Steroid therapy also has side effects that include elevation of intraocular pressure.

Undesired activity of phosphodiesterase 4 is present in the above-cited types of ocular disorders. Cyclic adenosine monophosphate (cAMP) is a known anti-inflammatory second messenger. Elevated cAMP levels inhibit leukocyte function and suppress cytokine production in a variety of cells, thereby reducing inflammation. Further, cAMP has been shown to stimulate lacrimal gland secretion and increase tear volume (Gilbard J P, et al., *IOVS* 31(7):1381-8, 1990).

Phosphodiesterase type-IV (PDE4 or PDE-IV) is the predominant cyclic nucleotide hydrolyzing enzyme found in inflammatory leukocytes, such as mast cells, neutrophils, monocytes and T-lymphocytes. PDE4 catalyzes the hydrolysis of cAMP, thereby reducing intracellular levels thereof which results in increased inflammatory activity.

Since PDE4 activity controls the levels of cAMP in inflammatory cells, inhibitors of this enzyme have anti-inflammatory activity and are useful therapeutic agents in reducing inflammatory processes contributing to the manifestations of dry eye and conjunctivitis. Elevation of cAMP by inhibition of phosphodiesterase has been shown to increase goblet cell secretion of mucin, stimulate lacrimal gland secretion and promote fluid secretion by ocular surface cells. Existing small molecule PDE4 inhibitors have been shown to suppress expression of proinflammatory cytokines, to stimulate secretion of mucins in human ocular surface epithelial cells, and to have efficacy in allergic inflammation and in uveitis.

Small molecule PDE4 inhibitors are not particularly potent and require high concentrations of drug with the attendant topical formulation difficulties. Further, inhibitors of phosphodiesterases vary in selectivity and specificity for individual enzymes and therefore can possess diverse pharmacological and toxicological properties.

The present invention provides highly selective inhibitors of PDE4 isoforms with the primary biological effect being suppression of inflammation.

SUMMARY OF THE INVENTION

The present invention is directed to interfering RNAs that silence phosphodiesterase type 4 (PDE4) mRNA expression, thus elevating cyclic AMP levels in patients with a cAMP-related ocular disorder or at risk of developing a cAMP-related ocular disorder. PDE4 targets include PDE4A, PDE4B, PDE4C, and PDE4D isoforms. The interfering RNAs of the invention are useful for treating patients with cAMP-related ocular disorders, particularly for patients with ocular inflammation, dry eye or conjunctivitis, or for patients at risk of developing ocular inflammation, dry eye or conjunctivitis.

An embodiment of the present invention provides a method of attenuating expression of a phosphodiesterase type 4 mRNA in a subject. The method comprises administering to the subject a composition comprising an effective amount of interfering RNA having a length of 19 to 49 nucleotides and a pharmaceutically acceptable carrier. In one embodiment, administration is to an eye of the subject for attenuating expression of a cAMP-related ocular disorder target in a human.

In one embodiment of the invention, the interfering RNA comprises a sense nucleotide strand, an antisense nucleotide strand and a region of at least near-perfect contiguous complementarity of at least 19 nucleotides. Further, the antisense strand hybridizes under physiological conditions to a portion of an mRNA corresponding to SEQ ID NO:1, SEQ ID NO:2, SEQ ID NO:3, or SEQ ID NO:4 which are sense cDNA sequences encoding PDE4A, PDE4B, PDE4C, and PDE4D, respectively (GenBank accession no. NM_006202, NM_002600, NM_000923, and NM_006203, respectively). The antisense strand has a region of at least near-perfect contiguous complementarity of at least 19 nucleotides with the hybridizing portion of mRNA corresponding to SEQ ID NO:1, SEQ ID NO:2, SEQ ID NO:3, or SEQ ID NO:4, respectively. The administration of such a composition attenuates the expression of a PDE4 target in the subject.

In one embodiment of the invention, an interfering RNA is designed to target an mRNA corresponding to SEQ ID NO:1 comprising nucleotide 374, 394, 395, 438, 496, 610, 611, 614, 654, 656, 821, 823, 824, 845, 868, 869, 871, 1052, 1058, 1082, 1132, 1175, 1295, 1325, 1448, 1818, 1859, 1865, 2735, 2736, 2737, 2738, 2745, 2855, 2887, 2889, 2895, 2898, 3320, 3328, 3832, 3833, 4164, 4166, 4189, 4190, 4193, 4195, 4204, 4216, 4217, or 4221.

In another embodiment of the invention, an interfering RNA is designed to target an mRNA corresponding to SEQ ID NO:2 comprising nucleotide 567, 568, 691, 709, 808, 871, 1089, 1242, 1316, 1324, 1768, 1776, 1789, 1801, 1803, 1804, 1810, 1860, 2070, 2071, 2105, 2185, 2208, 2596, 2645, 3281, 3298, 3299, 3377, 3485, 3569, 3744, 3745, 3790, 3827, 3879, 3949, 3950, 3960, 4033, 4046, 4050, 4051, 4092, 4093, or 4120.

In yet another embodiment of the invention, an interfering RNA is designed to target an mRNA corresponding to SEQ ID NO:3 comprising nucleotide 248, 469, 477, 550, 725, 812, 818, 975, 1147, 1247, 1309, 1379, 1442, 1444, 1445, 1448, 1622, 1695, 1696, 1697, 1712, 1869, 1871, 2069, 2142, 2144, 2164, 2231, 2373, 2560, 2570, 2582, 2777, 2778, 2779, or 2858.

In a further embodiment of the invention, an interfering RNA is designed to target an mRNA corresponding to SEQ ID NO:4 comprising nucleotide 190, 245, 259, 296, 318, 363, 364, 632, 1012, 1033, 1082, 1163, 1228, 1243, 1369, 1399, 1423, 1426, 1483, 1563, 1616, 1617, 1782, 1874, 1919, 1980, 2066, 2493, 2599, 3203, 3258, 3418, 3422, 3423, 3503, 3504, 3681, 3714, 4257, 4463, 4475, 4476, 4531, 4843, 4952, 5042, 5272, 5401, 5447, 5449, 5459, 5555, 5561, 5655, 5790, or 5801.

The present invention further provides for administering a second interfering RNA to a subject in addition to a first interfering RNA. The method comprises administering to the subject a second interfering RNA having a length of 19 to 49 nucleotides and comprising a sense nucleotide strand, an antisense nucleotide strand, and a region of at least near-perfect complementarity of at least 19 nucleotides; wherein the antisense strand of the second interfering RNA hybridizes under physiological conditions to a second portion of mRNA corresponding to SEQ ID NO:1, SEQ ID NO:2, SEQ ID NO:3, or SEQ ID NO:4 and the antisense strand has a region of at least near-perfect contiguous complementarity of at least 19 nucleotides with the second hybridizing portion of mRNA corresponding to SEQ ID NO:1, SEQ ID NO:2, SEQ ID NO:3, or SEQ ID NO:4, respectively. The second interfering RNA may target the same mRNA as the first interfering RNA or may target a different mRNA. Further, a third, fourth, or fifth, etc. interfering RNA may be administered in a similar manner.

Another embodiment of the invention is a method of attenuating expression of PDE4 in a subject comprising administering to the subject a composition comprising an effective amount of single-stranded interfering RNA having a length of 19 to 49 nucleotides and a pharmaceutically acceptable carrier.

For attenuating expression of PDE4A, the single stranded interfering RNA hybridizes under physiological conditions to a portion of mRNA corresponding to SEQ ID NO:1 comprising nucleotide 374, 394, 395, 438, 496, 610, 611, 614, 654, 656, 821, 823, 824, 845, 868, 869, 871, 1052, 1058, 1082, 1132, 1175, 1295, 1325, 1448, 1818, 1859, 1865, 2735, 2736, 2737, 2738, 2745, 2855, 2887, 2889, 2895, 2898, 3320, 3328, 3832, 3833, 4164, 4166, 4189, 4190, 4193, 4195, 4204, 4216, 4217, or 4221, and the interfering RNA has a region of at least near-perfect complementarity with the hybridizing portion of mRNA corresponding to SEQ ID NO:1. Expression of PDE4A is thereby attenuated.

For attenuating expression of PDE4B, the single stranded interfering RNA hybridizes under physiological conditions to a portion of mRNA corresponding to SEQ ID NO:2 comprising nucleotide 567, 568, 691, 709, 808, 871, 1089, 1242, 1316, 1324, 1768, 1776, 1789, 1801, 1803, 1804, 1810, 1860, 2070, 2071, 2105, 2185, 2208, 2596, 2645, 3281, 3298, 3299, 3377, 3485, 3569, 3744, 3745, 3790, 3827, 3879, 3949, 3950, 3960, 4033, 4046, 4050, 4051, 4092, 4093, or 4120, and the interfering RNA has a region of at least near-perfect contiguous complementarity with the hybridizing portion of mRNA corresponding to SEQ ID NO:2. Expression of PDE4B is thereby attenuated.

For attenuating expression of PDE4C, the single stranded interfering RNA hybridizes under physiological conditions to a portion of mRNA corresponding to SEQ ID NO:3 comprising nucleotide 248, 469, 477, 550, 725, 812, 818, 975, 1147, 1247, 1309, 1379, 1442, 1444, 1445, 1448, 1622, 1695, 1696, 1697, 1712, 1869, 1871, 2069, 2142, 2144, 2164, 2231, 2373, 2560, 2570, 2582, 2777, 2778, 2779, or 2858, and the interfering RNA has a region of at least near-perfect contiguous complementarity with the hybridizing portion of mRNA corresponding to SEQ ID NO:3. Expression of PDE4C is thereby attenuated.

For attenuating expression of PDE4D, the single stranded interfering RNA hybridizes under physiological conditions to a portion of mRNA corresponding to SEQ ID NO:4 comprising nucleotide 190, 245, 259, 296, 318, 363, 364, 632, 1012, 1033, 1082, 1163, 1228, 1243, 1369, 1399, 1423, 1426, 1483, 1563, 1616, 1617, 1782, 1874, 1919, 1980, 2066, 2493, 2599, 3203, 3258, 3418, 3422, 3423, 3503, 3504, 3681, 3714, 4257, 4463, 4475, 4476, 4531, 4843, 4952, 5042, 5272, 5401, 5447, 5449, 5459, 5555, 5561, 5655, 5790, or 5801, and the interfering RNA has a region of at least near-perfect contiguous complementarity with the hybridizing portion of mRNA corresponding to SEQ ID NO:4. Expression of PDE4D is thereby attenuated.

A further embodiment of the invention is a method of treating a cAMP-related ocular disorder in a subject in need thereof. The method comprises administering to an eye of the subject a composition comprising an effective amount of interfering RNA having a length of 19 to 49 nucleotides and a pharmaceutically acceptable carrier, the interfering RNA comprising a sense nucleotide strand, an antisense nucleotide strand, and a region of at least near-perfect contiguous complementarity of at least 19 nucleotides. The antisense strand hybridizes under physiological conditions to a portion of mRNA corresponding to SEQ ID NO:1, SEQ ID NO: 2, SEQ ID NO:3, or SEQ ID NO:4, and has a region of at least near-perfect contiguous complementarity of at least 19 nucleotides with the hybridizing portion of mRNA corresponding to SEQ ID NO:1, SEQ ID NO:2, SEQ ID NO:3, or SEQ ID NO:4, respectively. The cAMP-related ocular disorder is treated thereby.

Another embodiment of the invention is a method of treating a cAMP-related ocular disorder in a subject in need thereof, the method comprising administering to an eye of the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of a mRNA corresponding to any one of SEQ ID NO:5, SEQ ID NO:11-SEQ ID NO:199 and SEQ ID NO:205-SEQ ID NO:207, wherein the cAMP-related ocular disorder is treated thereby.

Another embodiment of the invention is a method of attenuating expression of a PDE4 target mRNA in a subject, comprising administering to the subject a composition comprising an effective amount of interfering RNA having a length of 19 to 49 nucleotides and a pharmaceutically acceptable carrier, where the interfering RNA comprises a region of at least 13 contiguous nucleotides having at least 90% sequence complementarity to, or at least 90% sequence identity with, the penultimate 13 nucleotides of the 3' end of a mRNA corresponding to any one of SEQ ID NO:5, SEQ ID NO:11-SEQ ID NO:199, and SEQ ID NO:205-SEQ ID NO:207 as follows.

When the target mRNA is PDE4A mRNA, the interfering RNA comprises a region of at least 13 contiguous nucleotides having at least 90% sequence complementarity to, or at least 90% sequence identity with, the penultimate 13 nucleotides of the 3' end of a mRNA corresponding to any one of SEQ ID NO:5, and SEQ ID NO:11-SEQ ID NO:61.

When the target mRNA is PDE4B mRNA, the interfering RNA comprises a region of at least 13 contiguous nucleotides having at least 90% sequence complementarity to, or at least 90% sequence identity with, the penultimate 13 nucleotides of the 3' end of a mRNA corresponding to any one of SEQ ID NO:62-SEQ ID NO:107.

When the target mRNA is PDE4C mRNA, the interfering RNA comprises a region of at least 13 contiguous nucleotides having at least 90% sequence complementarity to, or at least 90% sequence identity with, the penultimate 13 nucleotides of the 3' end of a mRNA corresponding to any one of SEQ ID NO:108-SEQ ID NO:143.

When the target mRNA is PDE4D mRNA, the interfering RNA comprises a region of at least 13 contiguous nucleotides having at least 90% sequence complementarity to, or at least 90% sequence identity with, the penultimate 13 nucleotides of the 3' end of a mRNA corresponding to any one of SEQ ID NO:144-SEQ ID NO:199 and SEQ ID NO:205-SEQ ID NO:207.

In a further embodiment of the present invention, the region of contiguous nucleotides is a region of at least 14 contiguous nucleotides having at least 85% sequence complementarity to, or at least 85% sequence identity with, the penultimate 14 nucleotides of the 3' end of a mRNA corresponding to the sequence of the sequence identifier. In yet another embodiment of the invention, the region of contiguous nucleotides is a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of a mRNA corresponding to the sequence identified by the sequence identifier.

A further embodiment of the invention is a method of treating a cAMP-related ocular disorder in a subject in need thereof, the method comprising administering to the subject a composition comprising a double stranded siRNA molecule that down regulates expression of a PDE4A, PDE4B, PDE4C or PDE4D gene via RNA interference, wherein each strand of the siRNA molecule is independently about 19 to about 27 nucleotides in length; and one strand of the siRNA molecule comprises a nucleotide sequence having substantial complementarity to an mRNA corresponding to the PDE4A, PDE4B, PDE4C or PDE4D gene, respectively, so that the siRNA molecule directs cleavage of the mRNA via RNA interference.

A composition comprising interfering RNA having a length of 19 to 49 nucleotides and having a nucleotide sequence of any one of SEQ ID NO:5, SEQ ID NO:11-SEQ ID NO:199, and SEQ ID NO:205-SEQ ID NO:207, or a complement thereof, and a pharmaceutically acceptable carrier is an embodiment of the present invention. In one embodiment, the interfering RNA is isolated. The term "isolated" means that the interfering RNA is free of its total natural mileau.

Another embodiment of the invention is a composition comprising a double stranded siRNA molecule that down regulates expression of a PDE4A, PDE4B, PDE4C or PDE4D gene via RNA interference, wherein each strand of the siRNA molecule is independently about 19 to about 27 nucleotides in length; and one strand of the siRNA molecule comprises a nucleotide sequence has substantial complementarity to an mRNA corresponding to the PDE4A, PDE4B, PDE4C or PDE4D gene, respectively, so that the siRNA molecule directs cleavage of the mRNA via RNA interference.

The present invention provides an advantage over small molecule inhibitors of phosphodiesterase type 4 since an undesirable side effect of current small molecule therapies can be avoided (e.g., increased intraocular pressure and cataract formation) and treatment is more specific. Further, interfering RNAs can have a longer duration of action and an optimized inhibition profile, i.e., preferential inhibition of isoforms that promote the inflammatory response with reduced inhibition of isoforms associated with adverse side effects.

Use of any of the embodiments as described herein in the preparation of a medicament for attenuating expression of PDE4A, PDE4B, PDE4C or PDE4D mRNA is also an embodiment of the present invention.

BRIEF DESCRIPTION OF THE FIGURES

In order that the manner in which the above recited and other enhancements and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which:

FIG. 1 provides a qRT-PCR analysis of PDE4D mRNA expression in HeLa cells transfected with PDE4D siRNAs SEQ ID NO:205, SEQ ID NO:206, SEQ ID NO:207, and SEQ ID NO:164, each at 10 nM, 1 nM, and 0.1 nM; a non-targeting control siRNA (NTC2) at 10 nM; and a buffer control (Null).

DETAILED DESCRIPTION OF THE INVENTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition.

As used herein, all percentages are percentages by weight, unless stated otherwise.

As used herein and unless otherwise indicated, the terms "a" and "an" are taken to mean "one", "at least one" or "one or more".

As used herein, a "fluid" is a continuous, amorphous substance whose molecules move freely past one another and that has the tendency to assume the shape of its container, for example, a liquid or a gas.

As used herein, the term "health care provider" is known in the art and specifically includes a physician, a person with authority to prescribe a medication (whether directly or indirectly), and a veterinarian. In certain embodiments, a health care provider includes an individual that provides a medication without prescription, such as in providing an over-the-counter medication.

As used herein, the terms "identifying subjects" and "diagnosing" are used interchangeably with regard to the detection of a "predisposition", "increased propensity", "risk", "increased risk", and the like.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of PDE4 target mRNA thus increasing cAMP levels in patients with a cAMP-related ocular disorder. PDE4 targets include isoforms A, B, C, and D (PDE4A, PDE4B, PDE4C, and PDE4D). According to the present invention, interfering RNAs provided exogenously or expressed endogenously effect silencing of PDE4 expression in ocular tissues.

"Cyclic AMP-related ocular disorder," as used herein, means conditions of the eye where cyclic AMP mediates the condition, particularly in inflammation. Cyclic AMP is a known anti-inflammatory second messenger; elevated cAMP levels inhibit leukocyte function and suppress cytokine production in a variety of cells, thereby reducing inflammation. A cyclic AMP-related ocular disorder includes conditions such as dry eye, conjunctivitis such as vernal keratoconjunctivitis (VKC), atopic keratoconjunctivitis (AKC), and giant papillary conjunctivitis (GPC); iritis, uveitis, episcleritis, scleritis, keratitis, endophthalmitis, blepharitis, and iatrogenic inflammatory conditions.

Genetic analyses indicate that the four PDE4 gene isoforms mediate distinct functions. Therefore, isoform-specific interfering RNAs as described herein are provided to reduce or eliminate isoform-specific side effects.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for PDE4A. The mRNA sequence is identical to the DNA sense strand sequence with the "T" bases replaced with "U" bases. Therefore, the mRNA sequence of PDE4A is known from SEQ ID NO:1, the mRNA sequence of PDE4B is known from SEQ ID NO:2, the mRNA sequence of PDE4C is known from SEQ ID NO:3, and the mRNA sequence of PDE4D is known from SEQ ID NO:4.

Phosphodiesterase 4 (PDE4A-PDE4D):

The PDE4 genes encode cyclic AMP (cAMP)-specific, cyclic nucleotide phosphodiesterases (PDE). Cyclic nucleotides are important second messengers that regulate and mediate a number of cellular responses to extracellular signals. The cyclic nucleotide phosphodiesterases (PDEs) regulate the cellular concentrations of cyclic nucleotides and thereby play a role in signal transduction. Phosphodiesterase 4, PDE4, catalyzes the specific hydrolysis of cAMP, thereby playing a role in the inflammatory response. There are at least 16 mammalian PDE4 isozymes or variants encoded by four distinct genes, PDE4A-PDE4D.

The GenBank database of the National Center for Biotechnology Information at ncbi.nlm.nih.gov provides the DNA sequence for PDE4A as accession no. NM_006202, provided in the "Sequence Listing" as SEQ ID NO:1. SEQ ID NO:1 provides the sense strand sequence of DNA that corresponds to the mRNA encoding PDE4A (with the exception of "T" bases for "U" bases). The coding sequence for PDE4A is from nucleotides 304-2247.

Equivalents of the above-cited PDE4A mRNA sequence are alternative splice forms, allelic forms, isozymes, or a cognate thereof. A cognate is a PDE4A mRNA from another mammalian species that is homologous to SEQ ID NO:1.

The GenBank database provides the DNA sequence for PDE4B as accession no. NM_002600, provided in the "Sequence Listing" as SEQ ID NO:2. SEQ ID NO:2 provides the sense strand sequence of DNA that corresponds to the mRNA encoding PDE4B (with the exception of "T" bases for "U" bases). The coding sequence for PDE4B is from nucleotides 147-2357.

Equivalents of the above-cited PDE4B mRNA sequence are alternative splice forms, allelic forms, isozymes, or a cognate thereof. A cognate is a PDE4B mRNA from another mammalian species that is homologous to SEQ ID NO:2.

The GenBank database provides the DNA sequence for PDE4C as accession no. NM_000923, provided in the "Sequence Listing" as SEQ ID NO:3. SEQ ID NO:3 provides the sense strand sequence of DNA that corresponds to the mRNA encoding PDE4C (with the exception of "T" bases for "U" bases). The coding sequence for PDE4C is from nucleotides 112-2250.

Equivalents of the above-cited PDE4C mRNA sequence are alternative splice forms, allelic forms, isozymes, or a cognate thereof. A cognate is a PDE4C mRNA from another mammalian species that is homologous to SEQ ID NO:3.

The GenBank database provides the DNA sequence for PDE4D as reference no. NM_006203, provided in the "Sequence Listing" as SEQ ID NO:4. SEQ ID NO:4 provides the sense strand sequence of DNA that corresponds to the mRNA encoding PDE4D (with the exception of "T" bases for "U" bases). The coding sequence for PDE4D is from nucleotides 75-2096.

Equivalents of the above-cited PDE4D mRNA sequence are alternative splice forms, allelic forms, isozymes, or a cognate thereof. A cognate is a PDE4D mRNA from another mammalian species that is homologous to SEQ ID NO:4.

Attenuating Expression of an mRNA:

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting one of the PDE4 targets is administered to elevate cAMP levels. In other embodiments, two or more interfering RNAs targeting the same PDE4 target (e.g., PDE4A) are administered to elevate cAMP levels. In still other embodiments, two or more interfering RNAs targeting different PDE4 targets (e.g., PDE4A and PDE4B) are administered to elevate cAMP levels.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of targets cited herein is also inferred in a human or mammal by observing an improvement in symptoms of the disorder, improvement in inflammation, an improvement in goblet cell secretion of mucin, an improvement in lacrimal gland secretion, or an improvement in ion fluid secretion by ocular surface cells, for example.

Interfering RNA:

In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, interfering RNA (e.g., siRNA) has a sense strand and an antisense strand, and the antisense strand comprises a region of at least near-perfect contiguous complementarity of at least 19 nucleotides to a target sequence of PDE4A, PDE4B, PDE4C, or PDE4D mRNA, and the sense strand comprises a region of at least near-perfect contiguous identity of at least 19 nucleotides with a target sequence of PDE4A, PDE4B, PDE4C, or PDE4D mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementary to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to a PDE4A, PDE4B, PDE4C, or PDE4D target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA.

An embodiment of a 19-nucleotide DNA target sequence for PDE4A mRNA is present at nucleotides 374 to 392 of SEQ ID NO:1:

5'-AAAGGATGTTGAACCGTGA-3' SEQ ID NO:5.

An siRNA of the invention for targeting a corresponding mRNA sequence of SEQ ID NO:5 and having 21-nucleotide strands and a 2-nucleotide 3' overhang is:

5'-AAAGGAUGUUGAACCGUGANN-3' SEQ ID NO:6
3'-NNUUUCCUACAACUUGGCACU-5' SEQ ID NO:7.

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:5 and having 21-nucleotide strands and a 3'UU overhang on each strand is:

5'-AAAGGAUGUUGAACCGUGAUU-3' SEQ ID NO:8
3'-UUUUUCCUACAACUUGGCACU-5' SEQ ID NO:9.

The interfering RNA may also have a 5' overhang of nucleotides or it may have blunt ends. An siRNA of the invention for targeting a corresponding mRNA sequence of SEQ ID NO:5 and having 19-nucleotide strands and blunt ends is:

5'-AAAGGAUGUUGAACCGUGA-3' SEQ ID NO:200
3'-UUUCCUACAACUUGGCACU-5' SEQ ID NO:201.

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:5 and having a 19 bp double-stranded stem region and a 3'UU overhang is:

SEQ ID NO: 10

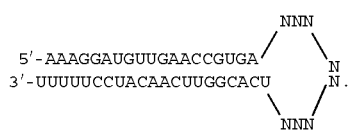

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:5) identified in the PDE4A DNA sequence (SEQ ID NO:1) by 6 nucleotides yields a 25-nucleotide DNA target sequence present at nucleotides 374 to 398 of SEQ ID NO:1:

5'-AAAGGATGTTGAACCGTGAGCTCAC-3' SEQ ID NO:202.

A dicer-substrate 27-mer duplex of the invention for targeting a corresponding mRNA sequence of SEQ ID NO:202 is:

5'-AAAGGAUGUUGAACCGUGAGCUCAC-3' SEQ ID NO:203
3'-UUUUUCCUACAACUUGGCACUCGAGUG-5' SEQ ID NO: 204.

The two nucleotides at the 3' end of the sense strand (i.e., the AC nucleotides of SEQ ID NO:203) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of PDE4A, PDE4B, PDE4C, and PDE4D DNA target sequences of SEQ ID NO:1, SEQ ID NO:2, SEQ ID NO:3, and SEQ ID NO:4, respectively, from which siRNAs of the present invention are designed in a manner as set forth above. PDE4A, PDE4B, PDE4C, and PDE4D encode phosphodiesterase isoforms IVA-IVD, as noted above.

TABLE 1

PDE4A, PDE4B, PDE4C, and PDE4D Target Sequences for siRNAs

| PDE4A Target Sequence | # of Starting Nucleotide with reference to Seq ID NO: 1 | SEQ ID NO: |
|---|---|---|
| AAAGGATGTTGAACCGTGA | 374 | 5 |
| CTCACACACCTGTCAGAAA | 394 | 11 |
| TCACACACCTGTCAGAAAT | 395 | 12 |
| AGAGTACATTTCCACAACA | 438 | 13 |
| ACGATGAAGGAACGAGAAA | 496 | 14 |
| ATGCATAGTAACAGCCTGA | 610 | 15 |
| TGCATAGTAACAGCCTGAA | 611 | 16 |
| ATAGTAACAGCCTGAACAA | 614 | 17 |
| GGTGAAGACCGATCAAGAA | 654 | 18 |
| TGAAGACCGATCAAGAAGA | 656 | 19 |
| TGGACACGATGGTGACATA | 821 | 20 |
| GACACGATGGTGACATACA | 823 | 21 |
| ACACGATGGTGACATACAT | 824 | 22 |
| TGACGCTGGAGGATCACTA | 845 | 23 |
| GCTGACGTGGCCTACCATA | 868 | 24 |
| CTGACGTGGCCTACCATAA | 869 | 25 |
| GACGTGGCCTACCATAACA | 871 | 26 |
| ATTCGGAGCTGGCGCTCAT | 1052 | 27 |
| AGCTGGCGCTCATGTACAA | 1058 | 28 |
| AGTCGGTGCTCGAGAATCA | 1082 | 29 |
| GAGGACAACTGCGACATCT | 1132 | 30 |
| GGCAGAGCCTACGCAAGAT | 1175 | 31 |
| TCCTCCTGCTAGATAACTA | 1295 | 32 |
| TCCAGGTCCTCCGGAACAT | 1325 | 33 |

TABLE 1-continued

PDE4A, PDE4B, PDE4C, and PDE4D Target Sequences for siRNAs

| | | |
|---|---|---|
| GCGAGCGTGGCATGGAAAT | 1448 | 34 |
| AGCTCTGGATGCAACCATA | 1818 | 35 |
| AGGAGTCGTTGGAAGTTAT | 1859 | 36 |
| CGTTGGAAGTTATGGCACA | 1865 | 37 |
| TCTAGAACGTGGTCAGGAA | 2735 | 38 |
| CTAGAACGTGGTCAGGAAT | 2736 | 39 |
| TAGAACGTGGTCAGGAATA | 2737 | 40 |
| AGAACGTGGTCAGGAATAG | 2738 | 41 |
| GGTCAGGAATAGCCATTCT | 2745 | 42 |
| AAAGTCTTCCGCTTGATTT | 2855 | 43 |
| CGATACTCCTGGCGATACT | 2887 | 44 |
| ATACTCCTGGCGATACTGA | 2889 | 45 |
| CTGGCGATACTGACTAGAA | 2895 | 46 |
| GCGATACTGACTAGAAAGT | 2898 | 47 |
| CCTAGGAGGAAGCAATAAT | 3320 | 48 |
| GAAGCAATAATGGTGTATA | 3328 | 49 |
| TGTAAGGTTGGTTTGTAAA | 3832 | 50 |
| GTAAGGTTGGTTTGTAAAT | 3833 | 51 |
| CTTGTGTATTGTCCACTTT | 4164 | 52 |
| TGTGTATTGTCCACTTTGA | 4166 | 53 |
| CAGTCATTCGGTCCGTTGA | 4189 | 54 |
| AGTCATTCGGTCCGTTGAT | 4190 | 55 |
| CATTCGGTCCGTTGATCAA | 4193 | 56 |
| TTCGGTCCGTTGATCAATA | 4195 | 57 |
| TTGATCAATAATCCTTCGA | 4204 | 58 |
| CCTTCGATCTTGTCTCCAA | 4216 | 59 |
| CTTCGATCTTGTCTCCAAT | 4217 | 60 |
| GATCTTGTCTCCAATTAAA | 4221 | 61 |

| PDE4B Target Sequence | # of Starting Nucleotide with reference to Seq ID NO: 2 | SEQ ID NO: |
|---|---|---|
| GACTATGACTTGTCACCAA | 567 | 62 |
| ACTATGACTTGTCACCAAA | 568 | 63 |
| ACTTCACTATACTGACAAA | 691 | 64 |
| ACCTTCATGGTACATCTAA | 709 | 65 |
| AAACGCTGGAGGAATTAGA | 808 | 66 |
| TCAGTGAGATGGCTTCTAA | 871 | 67 |
| ATGCATAGTTCAAGCCTAA | 1089 | 68 |
| TGCATCATGTATGCTATAT | 1242 | 69 |
| CTACATGATGACTTTAGAA | 1316 | 70 |
| TGACTTTAGAAGACCATTA | 1324 | 71 |
| CAGGCGTTCTTCTCCTAGA | 1768 | 72 |
| CTTCTCCTAGACAACTATA | 1776 | 73 |
| ACTATACCGATCGCATTCA | 1789 | 74 |
| GCATTCAGGTCCTTCGCAA | 1801 | 75 |
| ATTCAGGTCCTTCGCAACA | 1803 | 76 |
| TTCAGGTCCTTCGCAACAT | 1804 | 77 |
| TCCTTCGCAACATGGTACA | 1810 | 78 |
| TTGGAATTGTATCGGCAAT | 1860 | 79 |
| CTCGATACCTTAGAAGATA | 2070 | 80 |
| TCGATACCTTAGAAGATAA | 2071 | 81 |
| GAGCATGATACCTCAAAGT | 2105 | 82 |
| TTGAACTGACTCTCGATGA | 2185 | 83 |
| GATTCTGAAGGACCTGAGA | 2208 | 84 |
| CGATTCTGATCAAGACACA | 2596 | 85 |
| AGATCATTCTGCACTAAGT | 2645 | 86 |
| ACTGCCTTCTGCGCTAACA | 3281 | 87 |
| CACCTCCATTCCTGTTTAT | 3298 | 88 |
| ACCTCCATTCCTGTTTATA | 3299 | 89 |
| ATCTAACATTGCCTGCCAA | 3377 | 90 |
| GTCACTTAGTAGAGACATA | 3485 | 91 |
| AGTTGCTACTTCTGCACAA | 3569 | 92 |
| TTATAACTGGATCCTACTA | 3744 | 93 |
| TATAACTGGATCCTACTAT | 3745 | 94 |
| CACTACATTTGCTCACAGA | 3790 | 95 |
| CCGAACTACTGACTTTGAA | 3827 | 96 |
| GTCATGTTCCAGTTCATTA | 3879 | 97 |
| TGTAGCAAATTACGCAAAT | 3949 | 98 |
| GTAGCAAATTACGCAAATG | 3950 | 99 |
| ACGCAAATGTGAAGCCTCT | 3960 | 100 |
| GTTTCATGCTTTCAGTTCA | 4033 | 101 |
| AGTTCAGCATTGTGACTCA | 4046 | 102 |
| CAGCATTGTGACTCAGTAA | 4050 | 103 |
| AGCATTGTGACTCAGTAAT | 4051 | 104 |
| CATGACCAATGTATGTCTA | 4092 | 105 |
| ATGACCAATGTATGTCTAT | 4093 | 106 |
| CATTGTTTCAGGTGGACAT | 4120 | 107 |

| PDE4C Target Sequence | # of Starting Nucleotide with reference to Seq ID NO: 3 | SEQ ID NO: |
|---|---|---|
| TCTATTCGGATCCGGACAA | 248 | 108 |
| TTCCTGTACCGCTCAGATA | 469 | 109 |
| CCGCTCAGATAGCGACTAT | 477 | 110 |
| GGAGAGGACATGATTGTGA | 550 | 111 |
| TGGCATTGGAGACGCTAGA | 725 | 112 |
| CCAACAAGTTCAAGCGGAT | 812 | 113 |
| AGTTCAAGCGGATCCTGAA | 818 | 114 |
| CCGGATCAGTGGCCTACAT | 975 | 115 |
| CTCACAGCTATCATATTCA | 1147 | 116 |
| GTCACTACCACGCCAATGT | 1247 | 117 |
| ACGCATGTGCTGCTGGCTA | 1309 | 118 |
| TTGCAAGCGCCATCCACGA | 1379 | 119 |
| ACTCAGACGTGGCGCTTAT | 1442 | 120 |
| TCAGACGTGGCGCTTATGT | 1444 | 121 |
| CAGACGTGGCGCTTATGTA | 1445 | 122 |
| ACGTGGCGCTTATGTACAA | 1448 | 123 |
| ACATGAACCTCCTGGCCGA | 1622 | 124 |
| GGACAACTATTCCGACCGA | 1695 | 125 |
| GACAACTATTCCGACCGAA | 1696 | 126 |
| ACAACTATTCCGACCGAAT | 1697 | 127 |
| GAATCCAGGTCTTGCAGAA | 1712 | 128 |
| TGACAAGCATACGGCCTCA | 1869 | 129 |
| ACAAGCATACGGCCTCAGT | 1871 | 130 |
| CTGACAGATTCCAGTTTGA | 2069 | 131 |
| AGAGACAGCTTTAGCCAAA | 2142 | 132 |
| AGACAGCTTTAGCCAAAGA | 2144 | 133 |
| GCCTTGGAGTTGCCTGACA | 2164 | 134 |
| TCGACAACCAGAGGACTTA | 2231 | 135 |
| CAATCAAGCTCTTAGTTAT | 2373 | 136 |
| CCTCTCCAGTGGTCACTCT | 2560 | 137 |
| GGTCACTCTTGAGTCACAT | 2570 | 138 |
| GTCACATCTGTCACTTAAT | 2582 | 139 |
| AGCACCAAAGCTTCACTCA | 2777 | 140 |
| GCACCAAAGCTTCACTCAT | 2778 | 141 |
| CACCAAAGCTTCACTCATA | 2779 | 142 |
| GGCAAGGCATAGTGGCTTA | 2858 | 143 |

| PDE4D Target Sequence | # of Starting Nucleotide with reference to Seq ID NO: 4 | SEQ ID NO: |
|---|---|---|
| GGCTAATTCTCCAAGCAAA | 190 | 144 |
| TCGATCCGACAGCGATTAT | 245 | 145 |
| ATTATGACCTCTCTCCAAA | 259 | 146 |
| CTCCATTGCCAGTGATATA | 296 | 147 |
| GGAGATGACTTGATTGTGA | 318 | 148 |
| CTGCGAACTGTACGAAACA | 363 | 149 |
| TGCGAACTGTACGAAACAA | 364 | 150 |
| GAGTCGGTCTGGAAATCAA | 632 | 151 |
| TGACTCTCGAAGACCATTA | 1012 | 152 |
| ATGCTGATGTGGCCTATCA | 1033 | 153 |
| GTCTACTCATGTGCTATTA | 1082 | 154 |
| TGCAATACATGATGTAGAT | 1163 | 155 |
| TTGCCTTGATGTACAATGA | 1228 | 156 |
| ATGATTCCTCAGTCTTAGA | 1243 | 157 |
| ACATCGTACTTGCAACGAA | 1369 | 158 |
| ACATGAATCTACTGGCTGA | 1399 | 159 |
| AGACTATGGTTGAAACTAA | 1423 | 160 |
| CTATGGTTGAAACTAAGAA | 1426 | 161 |
| CCGATAGGATTCAGGTTCT | 1483 | 162 |
| CAGTGGACGGACCGGATAA | 1563 | 163 |
| GGAACGTGGCATGGAGATA | 1616 | 164 |
| GAACGTGGCATGGAGATAA | 1617 | 165 |
| GAATGGTACCAGGCACACA | 1782 | 166 |
| TGAACTAACTTTAGAGGAA | 1874 | 167 |
| CAGTGGCAGTCAAGTGGAA | 1919 | 168 |
| GACTCAGAGTCTACTGAAA | 1980 | 169 |
| TGTCATAGATGATCGTTCT | 2066 | 170 |
| ATGGACGAAGCAACAAATA | 2493 | 171 |

TABLE 1-continued

PDE4A, PDE4B, PDE4C, and PDE4D Target Sequences for siRNAs

| Sequence | Position | SEQ ID NO |
|---|---|---|
| CCTGATACATGACTGAATA | 2599 | 172 |
| CCTACTTAGTATCTCCTAA | 3203 | 173 |
| AGTGCATGTCTTTCTAATA | 3258 | 174 |
| TAGATGAGGTCTTGTCAAA | 3418 | 175 |
| TGAGGTCTTGTCAAATATA | 3422 | 176 |
| GAGGTCTTGTCAAATATAT | 3423 | 177 |
| ACCACGAGGTTGTATATCA | 3503 | 178 |
| CCACGAGGTTGTATATCAT | 3504 | 179 |
| AGAAACGGCTTTAAGTGTA | 3681 | 180 |
| TTAATGGACAGCCACATAA | 3714 | 181 |
| GCAAATGACTCATGCTGAA | 4257 | 182 |
| ACGTATGTTTGACCAAGTA | 4463 | 183 |
| CCAAGTAGTTTCACAAGAA | 4475 | 184 |
| CAAGTAGTTTCACAAGAAT | 4476 | 185 |
| TGAGTGAAGTCTAGAAAGA | 4531 | 186 |
| GGACTAATGCACTGTACAA | 4843 | 187 |
| TGGCTTTACATTTCCTAAA | 4952 | 188 |
| CATTTCAGCTTGCAAGTTA | 5042 | 189 |
| GTCTGTTTACAACCATGTA | 5272 | 190 |
| TGAATGGTGTGTATACATA | 5401 | 191 |
| ATATAGTCTTGTCACCTTA | 5447 | 192 |
| ATAGTCTTGTCACCTTAGA | 5449 | 193 |
| CACCTTAGAGCTTGTTTAT | 5459 | 194 |
| GGCTGTGCCTTAACTTTAA | 5555 | 195 |
| GCCTTAACTTTAACCAATA | 5561 | 196 |
| GATTAGAATTCTGCCAATA | 5655 | 197 |
| ATCTGTTGATCAGGAACTA | 5790 | 198 |
| AGGAACTACTTCAGCTACT | 5801 | 199 |
| GAAATCAAGTGTCAGAGTT | | 205 |
| GAACTTGCCTTGATGTACA | | 206 |
| CCAAGGAACTAGAAGATGT | | 207 |

As cited in the examples above, one of skill in the art is able to use the target sequence information provided in Table 1 to design interfering RNAs having a length shorter or longer than the sequences provided in Table 1 by referring to the sequence position in SEQ ID NO:1, SEQ ID NO:2, SEQ ID NO:3, or SEQ ID NO:4 and adding or deleting nucleotides complementary or near complementary to SEQ ID NO:1, SEQ ID NO:2, SEQ ID NO:3, or SEQ ID NO:4, respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of a mRNA corresponding to any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of a mRNA corresponding to the sequence identified by the sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of a mRNA corresponding to the sequence of the sequence identifier. Three nucleotide substitutions are included in such a phrase.

The target sequence in the mRNAs corresponding to SEQ ID NO:1, SEQ ID NO:2, SEQ ID NO:3, or SEQ ID NO:4 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense siRNA strand that is (are) not complementary to a portion of SEQ ID NO:1, SEQ ID NO:2, SEQ ID NO:3, or SEQ ID NO:4. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization under Physiological Conditions:

In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m° C. = 81.5 + 16.6(\log_{10}[Na+]) + 0.41$ (% G+C) − (600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-Stranded Interfering RNA:

As cited above, interfering RNAs ultimately function as single strands. Single-stranded (ss) interfering RNA has been found to effect mRNA silencing, albeit less efficiently than double-stranded RNA. Therefore, embodiments of the present invention also provide for administration of a ss interfering RNA that hybridizes under physiological conditions to a portion of SEQ ID NO:1, SEQ ID NO:2, SEQ ID NO:3 or SEQ ID NO:4 and has a region of at least near-perfect contiguous complementarity of at least 19 nucleotides with the hybridizing portion of SEQ ID NO:1, SEQ ID NO:2, SEQ ID NO:3, or SEQ ID NO:4 respectively. The ss interfering RNA has a length of 19 to 49 nucleotides as for the ds interfering RNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin Interfering RNA:

A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of Administration:

Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

Interfering RNA may be delivered directly to the eye by ocular tissue injection such as periocular, conjunctival, sub-tenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Subject:

A subject in need of treatment for a cAMP-related ocular disorder or at risk for developing a cAMP-related ocular disorder is a human or other mammal having a cAMP-related ocular disorder or at risk of having a cAMP-related ocular disorder associated with undesired or inappropriate expression or activity of targets as cited herein, i.e., PDE4A-D. Ocular structures associated with such disorders may include the eye, retina, choroid, lens, cornea, trabecular meshwork, iris, optic nerve, optic nerve head, sclera, anterior or posterior segment, or ciliary body, for example. A subject may also be an ocular cell, cell culture, organ or an ex vivo organ or tissue.

Formulations and Dosage:

Pharmaceutical formulations comprise interfering RNAs, or salts thereof, of the invention up to 99% by weight mixed with a physiologically acceptable carrier medium including those described infra, and such as water, buffer, saline, glycine, hyaluronic acid, mannitol, and the like.

Interfering RNAs of the present invention are administered as solutions, suspensions, or emulsions. The following are examples of possible formulations embodied by this invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

| | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

| | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |

-continued

| | Amount in weight % |
|---|---|
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNAs of embodiments of the invention results in an extracellular concentration at the surface of the target cell of from 100 pM to 1 μM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the target organ one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with interfering RNAs directed against any one of, or any combination of, PDE4A-D mRNA is expected to be beneficial over small molecule treatments by increasing the duration of action, thereby allowing less frequent dosing and greater patient compliance.

An effective amount of a formulation may depend on factors such as the age, race, and sex of the subject, the severity of the ocular hypertension, the rate of target gene transcript/protein turnover, the interfering RNA potency, and the interfering RNA stability, for example. In one embodiment, the interfering RNA is delivered topically to a target organ and reaches the PDE4A-D mRNA-containing tissue such as the trabecular meshwork, retina or optic nerve head at a therapeutic dose thereby ameliorating a cAMP-associated disease process.

Acceptable Carriers:

An acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Minis Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits:

Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also contains a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of interfering RNA to knock-down the levels of endogenous target gene expression in, for example, HeLa cells is evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, TAQMAN® forward and reverse primers and a probe set that preferably encompasses the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knockdown in target gene expression. Human corneal epithelial cells or other human ocular cell lines may also be use for an evaluation of the ability of interfering RNA to knock-down levels of an endogenous target gene.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

Example 1

Interfering RNA for Specifically Silencing PDE4D in HeLa Cells

The present study examines the ability of PDE4D-interfering RNA to knock down the levels of endogenous PDE4D protein expression in cultured HeLa cells.

Transfection of HeLa cells was accomplished using standard in vitro concentrations (0.1-10 nM) of PDE4D siRNAs or siCONTROL Non-targeting siRNA #2 (NTC2) and DHARMAFECT® #1 transfection reagent (Dharmacon, Lafayette, Colo.). All siRNAs were dissolved in 1×siRNA buffer, an aqueous solution of 20 mM KCl, 6 mM HEPES (pH 7.5), 0.2 mM $MgCl_2$. Control samples included a buffer control in which the volume of siRNA was replaced with an equal volume of 1×siRNA buffer (Null). PDE4D mRNA level was determined by qRT-PCR using Assays-On-Demand Gene Expression kits, TaqMan Universal PCR Master Mix, and an ABI PRISM 7700 Sequence Detector (Applied Biosystems, Foster City, Calif.). PDE4D mRNA expression was normalized to PPIB3 mRNA level, and was reported relative to PDE4D expression in non-transfected cells. The PDE4D siRNAs are double-stranded interfering RNAs having specificity for the following targets: siPDE4D #1 targets GAAATCAAGTGTCAGAGTT (SEQ ID NO:205); siPDE4D #2 targets GAACTTGCCTTGATGTACA (SEQ ID NO:206); siPDE4D #3 targets CCAAGGAACTAGAAGATGT (SEQ ID NO:207); siPDE4D #4 targets GAACGTGGCATGGAGATAA (SEQ ID NO:164). As shown by the data of FIG. 1, all four of the siRNAs caused a significant reduction in PDE4D mRNA expression at siRNA concentrations of 10 and 1 nM. However, siPDE4D #2 also silenced PDE4D expression significantly at 0.1 nM.

What is claimed is:

1. A method of attenuating expression of a PDE4 mRNA in an eye of a subject, the method comprising:

administering to an eye of the subject a composition comprising an effective amount of interfering RNA and a pharmaceutically acceptable carrier, the interfering RNA comprising a sense strand that is 19 nucleotides in length and is the corresponding mRNA sequence of SEQ ID NO: 108 or SEQ ID NO: 109, wherein the expression of the PDE4 mRNA is attenuated thereby.

2. The method of claim 1, wherein the subject has a cAMP-related ocular disorder.

3. The method of claim 1 wherein interfering RNA comprises a sense nucleotide strand and a antisense nucleotide strand connected by a hairpin loop.

4. The method of claim 1 wherein the interfering RNA is an shRNA, siRNA, or miRNA.

5. The method of claim 1 wherein the composition is administered via a topical, intravitreal, transcleral, periocular, conjunctival, subtenon, intracameral, subretinal, subconjunctival, retrobulbar, or intracanalicular route.

6. The method of claim 1 wherein the composition is administered via in vivo expression from an interfering RNA expression vector.

* * * * *